(12) United States Patent
Esbech et al.

(10) Patent No.: US 11,723,759 B2
(45) Date of Patent: Aug. 15, 2023

(54) DETECTING TOOTH SHADE

(71) Applicant: 3SHAPE A/S, Copenhagen (DK)

(72) Inventors: Bo Esbech, Gentofte (DK); Rune Fisker, Virum (DK); Lars Henriksen, Bagsvaerd (DK); Tais Clausen, Klagshamn (SE)

(73) Assignee: 3Shape A/S, Kobenhavn K (DK)

( * ) Notice: Subject to any disclaimer, the term of this patent is extended or adjusted under 35 U.S.C. 154(b) by 0 days.

(21) Appl. No.: 17/742,813

(22) Filed: May 12, 2022

(65) Prior Publication Data

US 2022/0265402 A1 Aug. 25, 2022

Related U.S. Application Data

(63) Continuation of application No. 16/946,186, filed on Jun. 9, 2020, which is a continuation of application No. 15/888,764, filed on Feb. 5, 2018, now Pat. No. 10,695,151, which is a continuation of application No. 15/117,078, filed as application No. PCT/EP2015/052537 on Feb. 6, 2015, now Pat. No. 10,010,387.

(51) Int. Cl.
| | |
|---|---|
| *A61C 19/10* | (2006.01) |
| *A61C 13/08* | (2006.01) |
| *G01J 3/50* | (2006.01) |
| *G16H 50/50* | (2018.01) |
| *G16H 20/40* | (2018.01) |

(52) U.S. Cl.
CPC ............ *A61C 13/082* (2013.01); *G01J 3/504* (2013.01); *G01J 3/508* (2013.01); *G16H 20/40* (2018.01); *G16H 50/50* (2018.01)

(58) Field of Classification Search
CPC .. A61C 13/0004; A61C 13/083; A61B 1/0615
See application file for complete search history.

(56) References Cited

U.S. PATENT DOCUMENTS

| | | |
|---|---|---|
| 3,878,905 A | 4/1975 | Schaumann |
| 3,971,065 A | 7/1976 | Bayer |

(Continued)

FOREIGN PATENT DOCUMENTS

| | | |
|---|---|---|
| CN | 1067573 A | 1/1993 |
| CN | 1906678 A | 1/2007 |

(Continued)

OTHER PUBLICATIONS

Jahne, et al., "Handbook of Computer Vision and Applications", Signal Processing and Pattern Recognition, Academic Press, vol. 2, 1999, 967 pages.

(Continued)

*Primary Examiner* — Yosef Kassa
(74) *Attorney, Agent, or Firm* — Buchanan Ingersoll & Rooney PC

(57) ABSTRACT

Disclosed in a method, a user interface and a system for use in determining shade of a patient's tooth, wherein a digital 3D representation including shape data and texture data for the tooth is obtained. A tooth shade value for at least one point on the tooth is determined based on the texture data of the corresponding point of the digital 3D representation and on known texture values of one or more reference tooth shade values.

15 Claims, 9 Drawing Sheets

(56) References Cited

U.S. PATENT DOCUMENTS

| | | |
|---|---|---|
| 4,291,958 A | 9/1981 | Frank et al. |
| 4,342,227 A | 8/1982 | Petersen et al. |
| 4,349,880 A | 9/1982 | Southgate et al. |
| 4,516,231 A | 5/1985 | Michaelis |
| 4,575,805 A | 3/1986 | Moermann et al. |
| 4,629,324 A | 12/1986 | Stern |
| 4,640,620 A | 2/1987 | Schmidt |
| 4,781,448 A | 11/1988 | Chatenever et al. |
| 4,802,759 A | 2/1989 | Matsumoto et al. |
| 4,896,015 A | 1/1990 | Taboada et al. |
| 5,131,844 A | 7/1992 | Marinaccio et al. |
| 5,151,609 A | 9/1992 | Nakagawa et al. |
| 5,181,181 A | 1/1993 | Glynn |
| 5,269,325 A | 12/1993 | Robinson et al. |
| 5,339,154 A | 8/1994 | Gassler et al. |
| 5,372,502 A | 12/1994 | Massen et al. |
| 5,377,011 A | 12/1994 | Koch |
| 5,381,236 A | 1/1995 | Morgan |
| 5,428,450 A | 6/1995 | Vieillefosse et al. |
| 5,455,899 A | 10/1995 | Forslund |
| 5,563,343 A | 10/1996 | Shaw et al. |
| 5,605,459 A | 2/1997 | Kuroda et al. |
| 5,615,003 A | 3/1997 | Hermary et al. |
| 5,675,407 A | 10/1997 | Geng |
| 5,702,249 A | 12/1997 | Cooper |
| 5,722,412 A | 3/1998 | Pflugrath et al. |
| 5,737,084 A | 4/1998 | Ishihara |
| 5,737,339 A | 4/1998 | Goto et al. |
| 5,766,006 A | 6/1998 | Murljacic |
| 5,850,289 A | 12/1998 | Fowler et al. |
| 5,851,113 A | 12/1998 | Jung et al. |
| 6,007,332 A | 12/1999 | O'Brien |
| 6,026,189 A | 2/2000 | Greenspan |
| 6,072,496 A | 6/2000 | Guenter et al. |
| 6,081,739 A | 6/2000 | Lemchen |
| 6,135,961 A | 10/2000 | Pflugrath et al. |
| 6,148,120 A | 11/2000 | Sussman |
| 6,206,691 B1 | 3/2001 | Lehmann et al. |
| 6,227,850 B1 | 5/2001 | Chishti et al. |
| 6,229,913 B1 | 5/2001 | Nayar et al. |
| 6,249,616 B1 | 6/2001 | Hashimoto |
| 6,251,073 B1 | 6/2001 | Imran et al. |
| 6,259,452 B1 | 7/2001 | Coorg et al. |
| 6,263,234 B1 | 7/2001 | Engelhardt et al. |
| 6,334,773 B1 | 1/2002 | Ahlen et al. |
| 6,334,853 B1 | 1/2002 | Kopelman et al. |
| 6,361,489 B1 | 3/2002 | Tsai |
| 6,450,807 B1 | 9/2002 | Chishti et al. |
| 6,471,511 B1 | 10/2002 | Chishti et al. |
| 6,476,803 B1 | 11/2002 | Zhang et al. |
| 6,485,413 B1 | 11/2002 | Boppart et al. |
| 6,532,299 B1 | 3/2003 | Sachdeva et al. |
| 6,575,751 B1 | 6/2003 | Lehmann et al. |
| 6,592,371 B2 | 7/2003 | Durbin et al. |
| 6,645,148 B2 | 11/2003 | Nguyen-Dinh et al. |
| 6,697,164 B1 | 2/2004 | Babayoff et al. |
| 6,743,014 B2 | 6/2004 | Kerschbaumer et al. |
| 6,750,873 B1 | 6/2004 | Bernardini et al. |
| 6,751,344 B1 | 6/2004 | Grumbine |
| 6,761,561 B2 | 7/2004 | Mandelkern et al. |
| 6,865,289 B1 | 3/2005 | Berestov |
| 6,904,159 B2 | 6/2005 | Porikli |
| 6,954,550 B2 | 10/2005 | Fujieda |
| 6,967,644 B1 | 11/2005 | Kobayashi |
| 6,975,898 B2 | 12/2005 | Seibel |
| 6,977,732 B2 | 12/2005 | Chen et al. |
| 6,990,228 B1 | 1/2006 | Wiles et al. |
| 7,010,223 B2 | 3/2006 | Thoms |
| 7,027,642 B2 | 4/2006 | Rubber et al. |
| 7,058,213 B2 | 6/2006 | Rubber et al. |
| 7,068,825 B2 | 6/2006 | Rubber et al. |
| 7,077,647 B2 | 7/2006 | Choi et al. |
| 7,079,679 B2 | 7/2006 | Kirk et al. |
| 7,086,863 B2 | 8/2006 | Van der Zel |
| 7,099,732 B2 | 8/2006 | Geng |
| 7,123,760 B2 | 10/2006 | Mullick et al. |
| 7,134,874 B2 | 11/2006 | Chishti et al. |
| 7,141,020 B2 | 11/2006 | Poland et al. |
| 7,156,655 B2* | 1/2007 | Sachdeva .............. A61C 9/0046 433/213 |
| 7,160,110 B2* | 1/2007 | Imgrund .............. G16H 20/30 433/167 |
| 7,166,537 B2 | 1/2007 | Jacobsen et al. |
| 7,184,150 B2 | 2/2007 | Quadling et al. |
| 7,197,179 B2 | 3/2007 | Rubbert et al. |
| 7,213,214 B2 | 5/2007 | Baar et al. |
| 7,215,430 B2 | 5/2007 | Kacyra et al. |
| 7,221,332 B2 | 5/2007 | Miller et al. |
| 7,230,771 B2 | 6/2007 | Kuiper et al. |
| 7,296,996 B2 | 11/2007 | Sachdeva et al. |
| 7,319,529 B2 | 1/2008 | Babayoff |
| 7,339,170 B2 | 3/2008 | Deliwala |
| 7,349,104 B2 | 3/2008 | Geng |
| 7,355,721 B2 | 4/2008 | Quadling et al. |
| 7,385,708 B2 | 6/2008 | Ackerman et al. |
| 7,458,812 B2 | 12/2008 | Sporbert et al. |
| 7,460,248 B2 | 12/2008 | Kurtz et al. |
| 7,471,821 B2 | 12/2008 | Rubbert et al. |
| 7,474,414 B2 | 1/2009 | Bae et al. |
| 7,483,062 B2 | 1/2009 | Allman et al. |
| 7,494,338 B2 | 2/2009 | Durbin et al. |
| 7,522,322 B2 | 4/2009 | Blanding et al. |
| 7,550,707 B2 | 6/2009 | Hashimoto et al. |
| 7,551,353 B2 | 6/2009 | Kim et al. |
| 7,605,817 B2 | 10/2009 | Zhang et al. |
| 7,609,875 B2 | 10/2009 | Liu et al. |
| 7,636,455 B2 | 12/2009 | Keaton et al. |
| 7,698,068 B2 | 4/2010 | Babayoff |
| 7,708,557 B2 | 5/2010 | Rubbert |
| 7,724,378 B2 | 5/2010 | Babayoff |
| 7,762,814 B2 | 7/2010 | van der Zel |
| 7,813,591 B2 | 10/2010 | Paley et al. |
| 7,831,292 B2 | 11/2010 | Quaid et al. |
| 7,840,042 B2 | 11/2010 | Kriveshko et al. |
| 7,929,151 B2 | 4/2011 | Liang et al. |
| 7,929,751 B2 | 4/2011 | Zhang et al. |
| 7,940,260 B2 | 5/2011 | Kriveshko |
| 7,946,845 B2 | 5/2011 | Lehmann |
| 8,003,889 B2 | 8/2011 | Turcovsky |
| 8,026,916 B2 | 9/2011 | Wen |
| 8,035,637 B2 | 10/2011 | Kriveshko |
| 8,078,006 B1 | 12/2011 | Sandrew et al. |
| 8,090,194 B2 | 1/2012 | Golrdon et al. |
| 8,092,215 B2 | 1/2012 | Stone-Collonge et al. |
| 8,103,134 B2 | 1/2012 | Sorek et al. |
| 8,121,351 B2 | 2/2012 | Katz et al. |
| 8,121,718 B2 | 2/2012 | Rubbert et al. |
| 8,144,954 B2 | 3/2012 | Quadling et al. |
| 8,177,551 B2* | 5/2012 | Sachdeva .............. A61C 9/0046 433/2 |
| 8,179,551 B2 | 5/2012 | Yamamichi |
| 8,180,100 B2 | 5/2012 | Fujimaki et al. |
| 8,208,704 B2 | 6/2012 | Wong et al. |
| 8,260,539 B2 | 9/2012 | Zeng |
| 8,280,152 B2 | 10/2012 | Thiel et al. |
| 8,331,653 B2 | 12/2012 | Seki et al. |
| 8,335,353 B2 | 12/2012 | Yamamoto et al. |
| 8,345,961 B2 | 1/2013 | Li et al. |
| 8,363,228 B2* | 1/2013 | Babayoff ........... A61B 1/00096 250/559.49 |
| 8,384,665 B1 | 2/2013 | Powers et al. |
| 8,386,061 B2 | 2/2013 | Violante et al. |
| 8,390,821 B2 | 3/2013 | Shpunt et al. |
| 8,400,635 B2 | 3/2013 | Inglese et al. |
| 8,442,283 B2 | 5/2013 | Choi |
| 8,451,456 B2* | 5/2013 | Babayoff ............... H04N 13/15 250/559.49 |
| 8,456,636 B2 | 6/2013 | Hennig |
| 8,469,705 B2 | 6/2013 | Sachdeva et al. |
| 8,477,320 B2 | 7/2013 | Stock et al. |
| 8,526,700 B2 | 9/2013 | Isaacs |
| 8,532,355 B2 | 9/2013 | Quadling et al. |
| 8,547,374 B1 | 10/2013 | Sadjadi et al. |
| 8,564,657 B2 | 10/2013 | Michalke et al. |

(56) References Cited

U.S. PATENT DOCUMENTS

| | | |
|---|---|---|
| 8,570,530 B2 | 10/2013 | Liang |
| 8,571,281 B2 | 10/2013 | Wong et al. |
| 8,571,397 B2 | 10/2013 | Liu et al. |
| 8,625,854 B2 | 1/2014 | Valkenburg et al. |
| 8,675,207 B2 | 3/2014 | Babayoff |
| 8,743,114 B2 | 6/2014 | Kim et al. |
| 8,828,287 B2 | 9/2014 | Van Der Zel |
| 8,848,991 B2 | 9/2014 | Tjioe et al. |
| 8,867,820 B2 | 10/2014 | Peeper et al. |
| 8,878,905 B2 | 11/2014 | Fisker et al. |
| 8,885,175 B2 | 11/2014 | Babayoff |
| 8,897,526 B2 | 11/2014 | Macleod et al. |
| 8,903,476 B2 | 12/2014 | Brennan et al. |
| 8,903,746 B2 | 12/2014 | Kudritskiy |
| 8,914,245 B2 | 12/2014 | Hopkins |
| 8,998,608 B2 * | 4/2015 | Imgrund ............... A61C 19/04 433/24 |
| 9,084,568 B2 * | 7/2015 | Katsumata ............... A61B 6/14 |
| 9,101,433 B2 | 8/2015 | Babayoff |
| 9,107,723 B2 | 8/2015 | Hall et al. |
| 9,173,727 B2 | 11/2015 | Yamamoto et al. |
| 9,185,388 B2 | 11/2015 | McNamer et al. |
| 9,208,531 B2 | 12/2015 | Boerjes et al. |
| 9,208,612 B2 | 12/2015 | Frahm et al. |
| 9,262,864 B2 | 2/2016 | Rohaly et al. |
| 9,299,192 B2 | 3/2016 | Kopelman |
| 9,322,646 B2 | 4/2016 | Pochiraju et al. |
| 9,329,675 B2 | 5/2016 | Ojelund et al. |
| 9,402,601 B1 | 8/2016 | Berger et al. |
| 9,404,740 B2 | 8/2016 | Babayoff |
| 9,456,963 B2 * | 10/2016 | Lee ........................ B33Y 70/10 |
| 9,554,692 B2 | 1/2017 | Levy |
| 9,554,857 B2 | 1/2017 | Toledo-Crow et al. |
| 9,566,138 B2 | 2/2017 | Fisker |
| 9,629,551 B2 | 4/2017 | Fisker et al. |
| 9,662,188 B2 | 5/2017 | Laubersheimer et al. |
| 9,675,432 B2 * | 6/2017 | Lee ........................ A61C 9/0006 |
| 9,707,061 B2 | 7/2017 | Morales et al. |
| 9,827,076 B2 | 11/2017 | Korten et al. |
| 9,844,430 B2 | 12/2017 | Morales et al. |
| 9,845,745 B2 | 12/2017 | Dudar |
| 9,861,457 B2 | 1/2018 | Fisker et al. |
| 9,962,246 B2 * | 5/2018 | Miller ................ A61C 13/0004 |
| 10,010,387 B2 * | 7/2018 | Esbech ................... G01J 3/508 |
| 10,064,553 B2 | 9/2018 | Fisker et al. |
| 10,097,815 B2 | 10/2018 | Fisker et al. |
| 10,111,714 B2 | 10/2018 | Kopelman et al. |
| 10,326,982 B2 | 6/2019 | Fisker et al. |
| 10,349,041 B2 | 7/2019 | Fisker et al. |
| 10,349,042 B1 | 7/2019 | Fisker et al. |
| 10,595,010 B2 | 3/2020 | Fisker et al. |
| 10,695,151 B2 | 6/2020 | Esbech et al. |
| RE48,221 E | 9/2020 | Ojelund et al. |
| 10,835,361 B2 * | 11/2020 | Fisker ................... A61B 5/1111 |
| 11,051,002 B2 | 6/2021 | Fisker et al. |
| 11,076,146 B1 | 7/2021 | Fisker et al. |
| 2001/0030748 A1 | 10/2001 | Jung et al. |
| 2003/0043089 A1 | 3/2003 | Hanson et al. |
| 2003/0096210 A1 | 5/2003 | Rubbert et al. |
| 2003/0156283 A1 | 8/2003 | Jung et al. |
| 2003/0158482 A1 | 8/2003 | Poland et al. |
| 2003/0164952 A1 | 9/2003 | Deichmann et al. |
| 2004/0080754 A1 | 4/2004 | Tobiason et al. |
| 2004/0125103 A1 | 7/2004 | Kaufman et al. |
| 2004/0155975 A1 | 8/2004 | Hart et al. |
| 2004/0185422 A1 | 9/2004 | Orth et al. |
| 2004/0204787 A1 | 10/2004 | Kopelman et al. |
| 2004/0254476 A1 | 12/2004 | Quadling et al. |
| 2005/0020910 A1 | 1/2005 | Quadling et al. |
| 2005/0057745 A1 | 3/2005 | Bontje |
| 2005/0074718 A1 | 4/2005 | Graham et al. |
| 2005/0090749 A1 | 4/2005 | Rubbert |
| 2005/0142517 A1 | 6/2005 | Frysh et al. |
| 2005/0212753 A1 | 9/2005 | Marvit et al. |
| 2005/0212756 A1 | 9/2005 | Marvit et al. |
| 2005/0232509 A1 | 10/2005 | Blake et al. |
| 2005/0237581 A1 | 10/2005 | Knighton et al. |
| 2005/0243330 A1 | 11/2005 | Magarill et al. |
| 2005/0283065 A1 | 12/2005 | Babayoff |
| 2006/0001739 A1 | 1/2006 | Babayoff |
| 2006/0020204 A1 | 1/2006 | Serra et al. |
| 2006/0025684 A1 | 2/2006 | Quistgaard et al. |
| 2006/0072123 A1 | 4/2006 | Wilson et al. |
| 2006/0072189 A1 | 4/2006 | DiMarzio et al. |
| 2006/0092133 A1 | 5/2006 | Touma et al. |
| 2006/0127852 A1 | 6/2006 | Wen |
| 2006/0146009 A1 | 7/2006 | Syrbe et al. |
| 2006/0158665 A1 | 7/2006 | Babayoff et al. |
| 2006/0212260 A1 | 9/2006 | Kopelman et al. |
| 2006/0251408 A1 | 11/2006 | Konno et al. |
| 2007/0016025 A1 | 1/2007 | Arenson et al. |
| 2007/0026363 A1 | 2/2007 | Lehmann et al. |
| 2007/0031774 A1 | 2/2007 | Cinader et al. |
| 2007/0041729 A1 | 2/2007 | Heinz et al. |
| 2007/0064242 A1 | 3/2007 | Childers |
| 2007/0078340 A1 | 4/2007 | Wilcox et al. |
| 2007/0081718 A1 | 4/2007 | Rubbert et al. |
| 2007/0103460 A1 | 5/2007 | Zhang et al. |
| 2007/0109559 A1 | 5/2007 | Babayoff et al. |
| 2007/0134615 A1 | 6/2007 | Lovely |
| 2007/0140539 A1 | 6/2007 | Katsumata et al. |
| 2007/0171220 A1 | 7/2007 | Kriveshko |
| 2007/0172112 A1 | 7/2007 | Paley et al. |
| 2007/0182812 A1 | 8/2007 | Ritchey |
| 2007/0194214 A1 | 8/2007 | Pfeiffer |
| 2007/0212667 A1 | 9/2007 | Jung et al. |
| 2007/0252074 A1 | 11/2007 | Ng et al. |
| 2008/0024768 A1 | 1/2008 | Babayoff |
| 2008/0058783 A1 | 3/2008 | Altshuler et al. |
| 2008/0063998 A1 | 3/2008 | Liang et al. |
| 2008/0070684 A1 | 3/2008 | Haigh-Hutchinson |
| 2008/0071143 A1 | 3/2008 | Gattani et al. |
| 2008/0118886 A1 | 5/2008 | Liang et al. |
| 2008/0131028 A1 | 6/2008 | Pillman et al. |
| 2008/0132886 A1 | 6/2008 | Cohen et al. |
| 2008/0194928 A1 | 8/2008 | Bandic et al. |
| 2008/0194950 A1 | 8/2008 | Mejia et al. |
| 2008/0316898 A1 | 12/2008 | Itoh et al. |
| 2009/0040175 A1 | 2/2009 | Xu et al. |
| 2009/0061381 A1 | 3/2009 | Durbin et al. |
| 2009/0076321 A1 | 3/2009 | Suyama et al. |
| 2009/0087050 A1 | 4/2009 | Gandyra |
| 2009/0097108 A1 | 4/2009 | Fox et al. |
| 2009/0103103 A1 | 4/2009 | Berner |
| 2009/0133260 A1 | 5/2009 | Durbin et al. |
| 2009/0160858 A1 | 6/2009 | Chen et al. |
| 2009/0167948 A1 | 7/2009 | Berman et al. |
| 2009/0177050 A1 | 7/2009 | Griffiths et al. |
| 2009/0217207 A1 | 8/2009 | Kagermeier et al. |
| 2009/0231649 A1 | 9/2009 | Sirat |
| 2009/0233253 A1 | 9/2009 | Mrazek |
| 2009/0279103 A1 | 11/2009 | Thiel et al. |
| 2009/0291417 A1 | 11/2009 | Rubbert et al. |
| 2009/0298017 A1 | 12/2009 | Boerjes et al. |
| 2009/0322676 A1 | 12/2009 | Kerr et al. |
| 2010/0009308 A1 | 1/2010 | Wen et al. |
| 2010/0079581 A1 | 4/2010 | Russell et al. |
| 2010/0085636 A1 | 4/2010 | Berner |
| 2010/0108873 A1 | 5/2010 | Schwertner |
| 2010/0156901 A1 | 6/2010 | Park et al. |
| 2010/0157086 A1 | 6/2010 | Segale et al. |
| 2010/0201986 A1 | 8/2010 | Inglese et al. |
| 2010/0231509 A1 | 9/2010 | Boillot et al. |
| 2010/0239136 A1 | 9/2010 | Gandyra et al. |
| 2010/0268069 A1 | 10/2010 | Liang |
| 2011/0125304 A1 | 5/2011 | Schneider et al. |
| 2011/0188726 A1 | 8/2011 | Nathaniel et al. |
| 2011/0200249 A1 | 8/2011 | Minear et al. |
| 2011/0310449 A1 | 12/2011 | Kim et al. |
| 2011/0316978 A1 | 12/2011 | Dillon et al. |
| 2012/0015316 A1 | 1/2012 | Sachdeva et al. |
| 2012/0062557 A1 | 3/2012 | Dillon et al. |
| 2012/0141949 A1 | 6/2012 | Bodony et al. |
| 2012/0179035 A1 | 7/2012 | Boudier |

(56) References Cited

U.S. PATENT DOCUMENTS

| | | | |
|---|---|---|---|
| 2012/0195471 A1 | 8/2012 | Newcombe et al. | |
| 2013/0034823 A1 | 2/2013 | Liang et al. | |
| 2013/0110469 A1 | 5/2013 | Kopelman | |
| 2013/0158694 A1 | 6/2013 | Rubbert et al. | |
| 2013/0218530 A1 | 8/2013 | Deichmann et al. | |
| 2013/0218531 A1 | 8/2013 | Deichmann et al. | |
| 2013/0244197 A1 | 9/2013 | Tjioe et al. | |
| 2013/0260340 A1* | 10/2013 | Stegall | A61B 6/145 433/217.1 |
| 2013/0335417 A1 | 12/2013 | McQueston et al. | |
| 2014/0022352 A1 | 1/2014 | Fisker et al. | |
| 2014/0022356 A1 | 1/2014 | Fisker et al. | |
| 2014/0146142 A1 | 5/2014 | Duret et al. | |
| 2014/0255878 A1 | 9/2014 | Jesenko et al. | |
| 2014/0377718 A1 | 12/2014 | Korten et al. | |
| 2015/0054922 A1 | 2/2015 | Fisker et al. | |
| 2016/0022389 A1 | 1/2016 | Esbech et al. | |
| 2016/0067018 A1 | 3/2016 | Korten et al. | |
| 2018/0153664 A1 | 6/2018 | Esbech et al. | |
| 2018/0255293 A1 | 9/2018 | Fisker et al. | |
| 2019/0124323 A1 | 4/2019 | Fisker et al. | |
| 2019/0200006 A1 | 6/2019 | Fisker et al. | |
| 2019/0289283 A1 | 9/2019 | Fisker et al. | |
| 2020/0169722 A1 | 5/2020 | Fisker et al. | |
| 2020/0352688 A1 | 11/2020 | Esbech et al. | |
| 2021/0211638 A1 | 7/2021 | Fisker et al. | |
| 2021/0306617 A1 | 9/2021 | Fisker et al. | |
| 2022/0086418 A1 | 3/2022 | Fisker et al. | |

FOREIGN PATENT DOCUMENTS

| | | |
|---|---|---|
| CN | 1934481 A | 3/2007 |
| CN | 101426085 A | 5/2009 |
| CN | 101513350 A | 8/2009 |
| DE | 19524855 A1 | 1/1997 |
| DE | 19642247 C1 | 1/1998 |
| DE | 10321863 A1 | 12/2004 |
| DE | 10321883 A1 | 12/2004 |
| DE | 102007005726 A1 | 8/2008 |
| DE | 102009023952 A1 | 12/2010 |
| EP | 0837659 A1 | 4/1998 |
| EP | 2200332 A1 | 6/2010 |
| EP | 2325771 A2 | 5/2011 |
| EP | 2620733 A1 | 7/2013 |
| EP | 2664272 A1 | 11/2013 |
| EP | 2799032 A1 | 11/2014 |
| JP | 62-100716 A | 5/1987 |
| JP | 06-505096 A | 6/1994 |
| JP | 06-201337 A | 7/1994 |
| JP | 3321866 B2 | 9/2002 |
| JP | 2004-029685 A | 1/2004 |
| JP | 2005-098833 A | 4/2005 |
| JP | 2007-072103 A | 3/2007 |
| JP | 2008-194108 A | 8/2008 |
| JP | 2009-098146 A | 5/2009 |
| JP | 2009-238245 A | 10/2009 |
| WO | 88/07695 A1 | 10/1988 |
| WO | 92/14118 A1 | 8/1992 |
| WO | 92/15034 A1 | 9/1992 |
| WO | 97/02788 A1 | 1/1997 |
| WO | 97/14932 A1 | 4/1997 |
| WO | 98/45745 A1 | 10/1998 |
| WO | 99/47964 A1 | 9/1999 |
| WO | 00/08415 A1 | 2/2000 |
| WO | 01/11193 A1 | 2/2001 |
| WO | 01/84479 A1 | 11/2001 |
| WO | 02/76327 A1 | 10/2002 |
| WO | 03/60587 A1 | 7/2003 |
| WO | 03/73457 A2 | 9/2003 |
| WO | 2004/066615 A1 | 8/2004 |
| WO | 2005/067389 A2 | 7/2005 |
| WO | 2006/065955 A2 | 6/2006 |
| WO | 2007/084727 A1 | 7/2007 |
| WO | 2008/125605 A2 | 10/2008 |
| WO | 2009/026645 A1 | 3/2009 |
| WO | 2009/034157 A1 | 3/2009 |
| WO | 2009/063088 A2 | 5/2009 |
| WO | 2009/089126 A1 | 7/2009 |
| WO | 2010/064156 A1 | 6/2010 |
| WO | 2010/106379 A1 | 9/2010 |
| WO | 2010/145669 A1 | 12/2010 |
| WO | 2011/011193 A1 | 1/2011 |
| WO | 2011/047731 A1 | 4/2011 |
| WO | 2011/120526 A1 | 10/2011 |
| WO | 2012/000511 A1 | 1/2012 |
| WO | 2012/007003 A1 | 1/2012 |
| WO | 2012/076013 A1 | 6/2012 |
| WO | 2012/083960 A1 | 6/2012 |
| WO | 2012/115862 A2 | 8/2012 |
| WO | 2013/010910 A1 | 1/2013 |
| WO | 2013/122662 A1 | 8/2013 |
| WO | 2014/125037 A1 | 8/2014 |

OTHER PUBLICATIONS

Jahne, et al., "Handbook of Computer Vision and Applications", System and Applications, vol. 3, Academic press, 1999, 955 pages.

Jerald Jason, "The VR Book: Human-Centered Design for Virtual Reality", (IPR2018-00197 Ex-2014), 2016, 4 pages.

Jethwa Manish, "Efficient Volumetric Reconstruction from Multiple Calibrated Cameras", PhD Thesis in Electrical Engineering and Computer Science at MIT, Sep. 2004, 143 pages.

Karatas et al., "Three-Dimensional Imaging Techniques: A Literature Review", European Journal of Dentistry, vol. 8 Issue 1, Jan.-Mar. 2014, pp. 132-140.

Kaufmann Hannes, "Applications of Mixed Reality", Thesis, Vienna University of Technology, May 27, 2009, 95 pages.

Li, et al., "Empty Space Skipping and Occlusion Clipping for Texture-based Volume Rendering", In IEEE Visualization (VIS'03), 2003, pp. 317-324.

Litomisky et al., "Removing Moving Objects from Point Cloud Scenes", Advances in Depth Image Analysis and Applications, Jan. 2013, pp. 1-10.

Litomisky, et al., "Removing moving objects from point cloud scenes", International Workshop on Depth Image Analysis and Applications, Springer, Bedin, Heidelberg, 2012, version listed at pdf.edu, pp. 1-10.

Liu, et al., "A Complete Statistical Inverse Ray Tracing Approach to Multi-View Stereo", In CVPR, IEEE, 2011, pp. 913-920.

Logozzo et al., "Recent Advances in Dental Optics—Part I: 3D Intraoral Scanners for Restorative Denistry", Optics and Lasers in Engineering, vol. 54, Mar. 2014, pp. 203-221 (1-19).

Lovi Davidi., "Incremental Free-Space Carving for Real-Time 3D Reconstruction", Master of Science Thesis in Computer Science at University of Alberta, 2011, 74 pages.

Mackinlay et al., "A Semantic Analysis of the Design Space of Input Devices", Human Computer Interaction, vol. 5, 1990, pp. 145-190.

Memorandum Order, *3Shape A/S v. Align Technology, Inc.*, C.A. No. 18-886-LPS, Exhibit 2022, Dec. 28, 2020, 3 pages.

Michael P. Keating "Geometric, Physical, and Visual Optics", Butterworth Publishers, 1988 (3 pages).

Montes et al., "An Overview of BRDF Models", University of Granada, 2012, pp. 1-26.

Moran et al., "A Comparison of the Imaging Performance of High Resolution Ultrasound Scanners for Preclinical Imaging", Ultrasound in Medicine & Biology, vol. 37, No. 3, Mar. 2011, pp. 493-501.

Myers Brada., "Graphical User Interface Programming", CRC Handbook of Computer Science and Engineering, 2d. Ed., Allen B. Tucker, Jan. 27, 2003, 30 pages.

Na Tanabe et al., "Telecentric Optics for Constant-Magnification Imaging", Department of Computer Science, Columbia University, Sep. 1995, 22 pages.

Nasiri Steven, "A Critical Review of MEMS Gyroscopes Technology and Commercialization Status", InvenSense, 2005, 8 pages.

Nitschke et al., "Real-Time Space Carving Using Graphics Hardware", IEICE Transactions on Information and Systems, Aug. 2007, pp. 1175-1184 (11 pages).

(56) References Cited

OTHER PUBLICATIONS

Noguchi et al., "Microscopic Shape from Focus Using a Projected Illumination Pattern", Mathematical and Computer Modelling, vol. 24, No. 5/6, Sep. 1996, pp. 31-48.
Notice of Opposition issued in corresponding European Patent No. 2 442 720, dated Aug. 24, 2016 (5 pages).
Notice of Opposition issued in corresponding European Patent No. 2 442 720, dated Aug. 24, 2016 (6 pages).
Notice of Opposition issued in corresponding European Patent No. 2 442 720, dated Jan. 16, 2019 (15 pages).
Notice of Opposition issued in corresponding European Patent No. 2 442 720, dated May 22, 2017 (41 pages).
Notice of Opposition issued in corresponding European Patent No. 2 442 720, dated May 24, 2017 (23 pages).
Notification of Information Statement dated Aug. 2, 2016, by the Japanese Patent Office in corresponding Japanese Patent Application No. 2014-234653 and English translation. (2 pages).
Notification of third party observations concerning JP 2014-234653 dated Oct. 27, 2015, and translation of notificatior (31 pages).
Ogami Moria, "Exhibit 2-3D Imagery Handbook", First Edition, Feb. 20, 2006, pp. 1-4.
Ojelund et al., "Inter Partes Review Certificate", U.S. Pat. No. 9,329,675 K1, 2 pages.
Ojelund Provisional, U.S. Appl. No. 61/420,138, filed Dec. 6, 2010, 45 pages.
Order, *Lipocine Inc.* v. *Glarus Therapeutics, Inc.*, C.A. No. 19-622 {WCB}, Exhibit 1052, Nov. 12, 2020, 2 pages.
Paris, et al. "A surface reconstruction method using global graph cut optimization", International Journal of Computer Vision, vol. 66. No. 2, HAL id: inria-00510219, 2010, pp. 141-161.
Patent Owne s Preliminary Response to the Petition for Inter Partes Review in IPR2018-00198, U.S. Pat. No. 9,329,675, dated Mar. 3, 2018, 66 pages.
Patent Owner's Preliminary Response to the Petition for Inter Partes Review of U.S. Pat. No. 10,349,042, *Align Technology, Inc.* v. *3Shape A/S*, Case No. IPR2020-01088 (dated Oct. 23, 2020), Exhibit 1062.
Patent Owner's Preliminary Response to the Petition for Inter Parties Review in IPR2018-00197, U.S. Pat. No. 9,329,675, dated Mar. 3, 2018, 66 pages.
Patent Owner's Response to the Petition for Inter Partes Review in IPR2018-00197, U.S. Pat. No. 9,329,675, dated Aug. 20, 2018, 57 pages.
Patent Owner's Submission of Demonstratives for Oral Argument in IPR2018-00197, U.S. Pat. No. 9,329,675, Jan. 31, 2019, 42 pages.
Petition for Inter Partes Review of U.S. Pat. No. 10,349,042, Case No. IPR2020-01087, *Align Technology, Inc.*, Petitioner, v. *3Shape A/S*, Patent Owner (89 pages).
Petition for Inter Partes Review of U.S. Pat. No. 10,349,042, Case No. IPR2020-01088, *Align Technology, Inc.*, Petitioner, v. *3Shape A/S*, Patent Owner (81 pages).
Petition for Inter Partes Review of U.S. Pat. No. 10,349,042, Case No. IPR2020-01089, *Align Technology, Inc.*, Petitioner, v. *3Shape A/S*, Patent Owner (76 pages).
Petition for Inter Partes Review of U.S. Pat. No. 8,363,228, *3Shape A/S et al.* v. *Align Technology, Inc.*, Case No. IPR2019-00154, Nov. 10, 2018, 100 pages.
Petition for Inter Partes Review of U.S. Pat. No. 8,363,228, *3Shape A/S et al.* v. *Align Technology, Inc.*, Case No. IPR2019-00157 (Nov. 8, 2018), Exhibit 1063.
Petitioner Align Technology, Inc.'s Demonstratives in IPR2018-00197, U.S. Pat. No. 9,329,675, Jan. 31, 2019, 30 pages.
Petitioner Align Technology, Inc.'s Reply to Patent Owner Response in IPR2018-00197, U.S. Pat. No. 9,329,675, dated Nov. 14, 2018, 35 pages.
Petitioner's Align Technology, Inc's Request for Rehearing in IPR20198-00198, U.S. Pat. No. 9,329,675, Jun. 29, 2018, 14 pages.

Plaintiff and Counterclaim Defendant Align Technology, Inc.'s Stipulation Regarding IPR2022-00144 and IPR2022-00145, Case No. 6:20-cv-00979 (W.D. Tex.), Dec. 16, 2021, 4 pages.
Pollard et al., "Change Detection in a 3-D World", IEEE Conference on Computer Vision and Pattern Recognition, Jun. 1, 2007, 6 pages.
Pulli, et al., "Surface Reconstruction and Display from Range and Color Data", Graphical Models, vol. 62, Issue 3, 2000, pp. 165-201.
3Shape A/S Markman Hearing Presentation, Case No. 1:18-886-LPS, Apr. 21, 2020, 104 pages.
*3Shape A/S* v. *Align Technology, Inc.*, IPR2021-01383, Petition for Inter Partes Review, U.S. Pat. No. 10,728,519, Aug. 20, 2021, 112 pages.
Ahn et al., "Development of Three-Dimensional Dental Scanning Apparatus Using Structured Illumination", Sensors, vol. 17, Issue 7, 1634 (IPR2018-00197, Ex. 2004) (IPR2018-00198, Ex. 2002), 2017, 9 pages.
*Align Technology, Inc.* Petitioner V., *3Shape A/S*, Patent Owner, Patent Owner's Preliminary Response Ot the Petition for Post-Grant Review of U.S. Pat. No. 9,962,244, Case No. PGR2018-00104, U.S. Pat. No. 9,962,244, filed Feb. 19, 2019, 64 pages.
*Align Technology, Inc.* Petitioner V., *3Shape A/S*, Patent Owner, Patent Owner's Preliminary Response to the Petition for Inter Partes Review of U.S. Pat. No. 9,962,244, Case No. IPR2018-00118, U.S. Pat. No. 9,962,244, filed Mar. 4, 2019, 62 pages.
*Align Technology, Inc.* Petitioner V., *3Shape A/S*, Patent Owner, Patent Owner's Preliminary Response to the Petition for Inter Partes Review of U.S. Pat. No. 9,962,244, Case No. IPR2019-00117, U.S. Pat. No. 9,962,244, filed Mar. 4, 2019, 63 pages.
*Align Technology, Inc.* Petitioner v., *3Shape A/S*, Patent Owner, Patent Owner's Preliminary Response to the Petition for Inter Partes Review of U.S. Pat. No. 9,962,244, Case No. IPR2019-00118, U.S. Pat. No. 9,962,244, filed Mar. 4, 2019, 62 pages.
*Align Technology, Inc.* Petitioner V., *3Shape A/S*, Patent Owner, Patent Owner's Preliminary Response to the Petition for Post-Grant Review of U.S. Pat. No. 9,962,244, Case No. PGR2018-00103, U.S. Pat. No. 9,962,244, filed Feb. 19, 2019, 64 pages.
*Align Technology, Inc.* Petitioner V., *3Shape A/S*, Patent Owner, Petition for Inter Partes Review of U.S. Pat. No. 9,962,244, Case No. IPR2019-00117, U.S. Pat. No. 9,962,244, filed Nov. 5, 2018, 98 pages.
*Align Technology, Inc.* Petitioner V., *3Shape A/S*, Patent Owner, Petition for Inter Partes Review of U.S. Pat. No. 9,962,244, Case No. IPR2019-00118, U.S. Pat. No. 9,962,244, filed Nov. 5, 2018, 93 pages.
*Align Technology, Inc.* Petitioner V., *3Shape A/S*, Patent Owner, Petition for Post-Grant Review of U.S. Pat. No. 9,962,244, Case No. PGR2018-00103, U.S. Pat. No. 9,962,244, filed Oct. 30, 2018, 119 pages.
*Align Technology, Inc.* Petitioner V., *3Shape A/S*, Patent Owner, Petition for Post-Grant Review of U.S. Pat. No. 9,962,244, Case No. PGR2018-00104, U.S. Pat. No. 9,962,244, filed Oct. 26, 2018, 107 pages.
*Align Technology, Inc.* Petitioner V., *3Shape A/S*, Patent Owner, Petition for Post-Grant Review of U.S. Pat. No. 9,962,244, Case No. PGR2019-00104, U.S. Pat. No. 9,962,244, filed Oct. 26, 2018, 107 pages.
Align Technology, Inc. Petitioner, Declaration of Dr. Chandrajit L. Bajaj, Ph.D. in Support of Inter Partes Review of U.S. Pat. No. 9,962,244, Case Nos. IPR2019-00117 U.S. Pat. No. 9,962,244, 3Shape A/S Patent Owner, filed Nov. 5, 2018, 316 pages.
Align Technology, Inc. Petitioner, Declaration of Dr. Chandrajit L. Bajaj, Ph.D. in Support of Inter Partes Review of U.S. Pat. No. 9,962,244, Case Nos. IPR2019-00118 U.S. Pat. No. 9,962,244, 3Shape A/S Patent Owner, filed Nov. 5, 2018, 316 pages.
Align Technology, Inc. Petitioner, Declaration of Dr. Chandrajit L. Bajaj, Ph.D. In Support of Post-Grant Review of U.S. Pat. No. 9,962,244, Case Nos. PGR2018-00103 U.S. Pat. No. 9,962,244, 3Shape A/S Patent Owner, filed Oct. 30, 2018, 318 pages.
Align Technology, Inc. Petitioner, Declaration of Dr. Chandrajit L. Bajaj, Ph.D. in Support of Post-Grant Review of U.S. Pat. No. 9,962,244, Case Nos. PGR2018-00104 U.S. Pat. No. 9,962,244, 3Shape A/S Patent Owner, filed Oct. 26, 2018, 318 pages.

(56) References Cited

OTHER PUBLICATIONS

Align Technology, Inc. Petitioner, Second Corrected Declaration of Dr. Chandrajit L. Bajaj, Ph.D. in Support of Post-Grant Review of U.S. Pat. No. 9,962,244,Case No. PGR2018-00103 U.S. Pat. No. 9,962,244, 3Shape A/S Patent Owner, filed Oct. 30, 2018, 318 pages.
Align Technology, Inc. Petitioner, Second Corrected Petition for Post-Grant Review of U.S. Pat. No. 9,962,244, Case No. PGR2018-00103 U.S. Pat. No. 9,962,244, 3Shape A/S Patent Owner, filed Oct. 30, 2018, 119 pages.
*Align Technology, Inc.*, Petitioner v. *3Shape A/S* Patent Owner, Case IPR2018-00197—U.S. Pat. No. 9,329,675, Decision Institution of Inter Partes Review, May 30, 2018, 32 pages.
*Align Technology, Inc.*, Petitioner v. *3Shape A/S* Patent Owner, Case IPR2018-00197—U.S. Pat. No. 9,329,675, Petition for Inter Partes Review, Nov. 22, 2017, 67 pages.
*Align Technology, Inc.*, Petitioner v. *3Shape A/S* Patent Owner, Case IPR2018-00198—U.S. Pat. No. 9,329,675, Decision Denying Institution of Inter Partes Review, May 30, 2018, 15 pages.
*Align Technology, Inc.*, Petitioner v. *3Shape A/S* Patent Owner, Case IPR2018-00198—U.S. Pat. No. 9,329,675, Petition for Inter Partes Review, Nov. 22, 2017, 78 pages.
Amended Complaint, *3Shape A/S* v. *Align Technology, Inc.*, Case No. 1:18-886-LPS, Aug. 30, 2019, 166 pages.
Answer, Affirmative Defenses, and Counterclaims of Align Technology, Inc., *3Shape A/S* v. *Align Technology, Inc.*,C.A. No 18-886-LPS, Oct. 21, 2019, 46 pages.
Atieh Mohammada., "Accuracy Evlaution of Intral-Oral Optical Impressions: A Novel Approach", Thesis, University of North Carolina at Chapel Hill, 2016, 87 pages.
Bajaj, Declaration of Dr. Chandrajit L. Bajaj, Ph.D., 3Shape A/S, Patent Owner, in Support of Inter Partes Review of U.S. Pat. No. 9,329,675, Case IPR2018-00197, 127 Pages.
Bernardini, et al., "High-Quality Texture Reconstruction from Multiple Scans", IEEE Transactions on Visualization and Computer Graphics, vol. 7, No. 4, Oct.-Dec. 2001, pp. 318-332.
Birnbaum et al., "Dental Impressions Using 3D Digital Scanners: Virtual Becomes Reality", Compendium of Continuing Education in Dentistry, vol. 29, No. 8, Oct. 2008, 18 pages.
Bob Johnstone, "Cameras give semiconductor industry a boost", New Scientist, Nov. 7, 1985 (1 page).
Bornik et al., "A Hybrid User Interface for Manipulation of Volumetric Medical Data", 3D User Interfaces, 2006, pp. 29-36 (8 pages).
Bowman et al., "3D User Interfaces Theory and Practice§ 4.1.1 "Input Device Characteristics" pp. 88-89; § 4.2.2 "2D Mice and Trackballs" pp. 91-92; § 4.8.2 "Input Device Taxonomies" pp. 128-132", Addison Wesley (IPR2018-00197, Ex. 2013), 2005, 20 pages.
Bowman et al., "3D User Interfaces: Theory and Practice", 2004, pp. 96-101, (IPR2018-00197, Ex. 1038) Jul. 2004, pp. 96-101 (9 pages).
Broadbent, B.H., "A New X-Ray Technique and Its Application to Orthodontia," The Angle Orthodontist, vol. 1, No. 2, 1931, pp. 45-66.
Broadhurst et al., "A Probabilistic Framework for Space Carving", Proceedings Eighth IEEE International Conference on Computer Vision, vol. 1, 2001, 6 pages.
Callier et al., "Reconstructing Textured Meshes From Multiple Range+rgb Maps", 7th International Fall Workshop on Vision, Modeling, and Visualization, Nov. 2002,, 8 pages.
Certified copy of Swiss Priority Document 01580/08, Oct. 6, 2008, with English Translation.
Chen, et al., "A Volumetric Stereo Matching Method: Application to Image-Based Modeling", IEEE Computer Society Conference on Computer Vision and Pattern Recognition (Cat. No. PR00149). vol. 1, 1999, 6 pages.
Chua et al., "SonoDEX: 3D Space Management and Visualization of Ultrasound Data", International Congress Series, vol. 1281, (IPR2018-00197, Ex. 2006), May 2005, pp. 143-148.

Corrected Declaration of Dr. Chandrajit L. Bajaj, Ph.D. in Support of Post-Grant Review of U.S. Pat. No. 9,962,244, Align Technology, Inc. Petitioner, Case Nos. PGR2018-00103 U.S. Pat. No. 9,962,244, 3Shape A/S Patent Owner, filed Oct. 30, 2018, 318 pages.
Curriculum Vitae of Dr. Chandrajit L. Bajaj, (IPR2018-00197, Ex. 1004) (IPR2018-00198, Ex. 1004), 49 pages.
Curriculum Vitae of Ravin Balakrishanan Ph.D. (IPR2018-00197, EX.2012), 30 pages.
Darrell et al., "Pyramid Based Depth from Focus", Proceedings CVPR '88: The Computer Society Conference on Computer Vision and Pattern Recognition, 1988, pp. 504-509.
Decision Denying Petitioner's Request for Rehearing in IPR20198-00198, U.S. Pat. No. 9,329,675, Dec. 4, 2018, 8 pages.
Declaration of Alexander Sergienko, PhD. in *3Shape A/S et al.* v. *Align Technology, Inc.*, Case No. IPR2020-01622, Exhibit 1061.
Declaration of Alexander Sergienko, Ph D., *Align Technology, Inc.* v. *3Shape A/S*, Case No. IPR2020-01087, Exhibit 2019.
Declaration of Dr. Chandrajit Bajaj ("Bajaj Deel.") in support of Petition for Inter Partes Review, U.S. Pat. No. RE48,221, 377 pages.
Declaration of Lambertus Hesselink, Ph.D., Exhibit 1002.
Declaration of Ravin Balakrishanan, (IPR2018-00197, EX.2011), 55 pages.
Declaration of Sylvia Hall-Ellis, Ph.D. with attachments, *Align Technology, Inc.* v. *3Shape A/S*, Case No. IPR2020-01087, Exhibit 2029.
Defendant Align Technology, Inc.'s Initial Invalidity Contentions, *3Shape A/S* v. *Align Technology, Inc.*, C.A. No. 1:18-cv-00886-LPS, Nov. 21, 2017, 393 pages.
Defendant Align Technology, Inc.'s Stipulation of Invalidity Contentions, *3Shape A/S* v. *Align Technology, Inc.*, C.A. No. 18-886-LPS, Exhibit 1053, Nov. 13, 2020, 3 pages.
Defendant's Identification of Invalidity References, *3Shape A/S*, Plaintiff, v. *Align Technology, Inc.*, Defendant, C.A. No. 1:18-CV-00886-LPS, in the United States District Court for the District of Delaware. (72 pages).
Deposition Transcript of Chandrajit Bajaj, Ph.D with Errata Sheet, (IPR2018-00197 Ex-2008), Jul. 25, 2018, 142 pages.
Deposition Transcript of Dr. Lambertus Hesselink taken Apr. 2, 2021, Exhibit 2023.
Deposition Transcript of Dr. Lambertus Hesselink taken Sep. 10, 2021, Exhibit 2030.
Deposition Transcript of Dr. Ravin Balakrishnan, Nov. 5, 2018, 101 pages.
Eisert et al., "Automatic Reconstruction of Stationary 3-D Objects from Multiple Uncalibrated Camera Views", IEEE Transactions on Circuits and Systems for Video Technology, vol. 10, No. 2, Mar. 2000, pp. 261-277.
Eisert, "Reconstruction of Volumetric 3D Models", 3D Videocommunication: Algorithms, Concepts and Real-Time Systems in Human Centered Communication, John Wiley & Sons, Ltd., 2001, 20 pages.
Eisert, et al., "Multi-Hypothesis, Volumetric Reconstruction of 3 D Objects From Multiple Calibrated Camera Views", CASSP'99, Phoenix, USA, Mar. 1999, pp. 3509-3512.
Elgammal, "CS 534: Computer Vision Texture," Department of Computer Science, Rutgers University, (Spring 2003). (22 pages).
EPO Prosecution History dated Jun. 19,2013, issued in the European Patent Application No. 11847582.1, 180 pages.
Exhibit 6—Latest Optical 3D MeasurementaL Nov. 20, 2006, pp. 1-16.
File History (IPR2018-00197, Ex. 1002) (IPR2018-00198, Ex. 1002), U.S. Pat. No. 9,329,675, 625 pages.
File History, U.S. Patent No. RE48,221, 1004 pages.
Final Written Decision—Termination Decision Document from IPR2018-00197, U.S. Pat. No. 9,329,675 B2, dated May 29, 2019, 64 pages.
Final Written Decision, *Align Technology, Inc.* v. *3Shape A/S*, IPR2020-01087, dated Jan. 19, 2022.
First Office Action dated Apr. 3, 2015, issued in the corresponding Chinese Patent Application No. 201180066956.6, 13 pages.
First Office Action dated Dec. 2, 2016, issued in the corresponding Chinese Patent Application No. 201510098304.0, 15 pages including 8 pages of English Translation.

(56) References Cited

OTHER PUBLICATIONS

First Office Action dated Feb. 20, 2014, issued in the corresponding Chinese Patent Application No. CN201080027248.7, 22 pages including 13 pages of English Translation.
Fisher, et al., "Dictionary of Computer Vision & Image Processing", Wiley, Second Edition, 2014, 386 pages.
Fisker et al., "Focus Scanning Apparatus", U.S. Appl. No. 61/187,744, filed Jun. 17, 2009, 90 pages.
Fisker et al., "Focus Scanning Apparatus", U.S. Appl. No. 61/231,118, filed Aug. 4, 2009, 127 pages.
Foley et al., "Introduction to Computer Graphics", Addison-Wesley, Chapter 2.2: Basic Interaction Handling, "Chapter 6: Viewing in 3D," and Chapter 8: Input Devices, Interaction Techniques, and Interaction Tasks, 1994, 66 pages.
Forne Christopher j., "3-D Scene Reconstruction From Multiple Photometric Images", PhD Thesis in Electrical and Computer Engineering at the University of Canterbury, Christchurch, NeW Zealand, Apr. 30, 2007, 179 pages.
Fraser et al., "Zoom-Dependent Camera Calibration in Digital Close-Range Photogrammetry", Photogrammetric Engineering & Remote Sensing, vol. 72, No. 9, Exhibit 1064, Sep. 2006, pp. 1017-1026.
Gao et al., "3D Shape Reconstruction of Teeth by Shadow Speckle Correlation Method", Optics and Lasers in Engineering, vol. 44, 2006, pp. 455-465.
Gehrung et al., "An Approach to Extract Moving Objects From MLS Data Using a Volumetric Background Representation", ISPRS Annals of the Photogrammetry, Remote Sensing and Spatial Information Sciences, vol. IV-1/W1, Jun. 2017, pp. 107-114.
Giammanco et al., "Using 3D Laser Scanning Technology to Create Digital Models of Hailstones", American Meteorological Society, Jul. 2017, pp. 1341-1347 (8 pages).
Gmitro et al., "Confocal Microscopy through a Fiber-Optic Imaging Bundle", Optics Letters, vol. 18, No. 8, Apr. 15, 1993, pp. 565-567 (4 pages).
Graetzel et al., "A Non-Contact Mouse for Surgeon-Computer Interaction", Technology and Health Care, vol. 12, No. 3, 2004, pp. 245-257.
Grant et al., "Glossary of Digital Dental Terms: American College of Prosthodontists", Journal of Prosthodontics, vol. 25, Suppl. 2, Oct. 2016, pp. S2-S9.
Guan et al., "Multi-view Occlusion Reasoning for Probabilistic Silhouette-Based Dynamic Scene Reconstruction", International Journal of Computer Vision, vol. 90, 2010, pp. 283-303.
Guehring Jens, "Dense 3D Surface Acquisition by Structured Light using off-the-Shelf Components", Proceedings SPIE 4309, Videometrics and Optical Methods for 3D Shape Measurement, Dec. 22, 2000, pp. 220-231 (13 pages).
Hajeer et al., "Current Products and Practices Applications of 3D Imaging in Orthodontics: Part II", Journal of Orthodontics, vol. 31, 2004, pp. 154-162.
Hale et al., "Measuring Free-Living Physical Activity in Adults with and Without Neurologic Dysfunction with a Triaxial Accelerometer", Archives of Physical Medicine and Rehabilitation, vol. 89, No. 9, Sep. 2008, pp. 1765-1771.
Havemann et al., "Seven Research Challenges of Generalized 3D Documents", IEEE Computer Graphics and Applications, vol. 27, No. 3, May-Jun. 2007, pp. 70-76.
Hearn et al., "Computer Graphics", 2d. Ed., Prentice Hall, Chapter 2: Overview of Graphics Systems, "Chapter 8: Graphical User Interfaces and Interactive Input Methods," and "Chapter 9: Three-Dimensional Concepts", 1994, 83 pages.
Horn, et al., "Calculating the Reflectance Map", Applied Optic, vol. 18, No. 11, Jun. 1979, pp. 1770-1779.
IEEE Xplore Search Results (4 pages), accessed Mar. 2, 2018; this document was made of record by the Examiner on Mar. 13, 2018, in the parent application (U.S. Appl. No. 15/117,078).
Information Statement issued on Jul. 28, 2016, by the Japanese Patent Office in corresponding Japanese Patent Application No. 2014-234653 and English translation. (25 pages).
Institution Decision entered in IPR20198-00197, U.S. Pat. No. 9,329,675, May 30, 2018, 32 pages.
International Preliminary Reporton Patentability received for PCT Patent Application No. PCT/DK2010/050148, dated Jan. 5, 2012, 10 page.
International Preliminary Reporton Patentability received for PCT Patent Application No. PCT/EP2015/052537, dated Aug. 18, 2016, 11 pages.
International Search Report (PCT/ISA/210) dated Feb. 22, 2012, issued in the International Patent Application No. PCT/DK2011/050461, 6 pages.
International Search Report and Written Opinion received for PCT Patent Application No. PCT/DK2010/050148, dated Oct. 6, 2010, 13 pages.
International Search Report and Written Opinion received for PCT Patent Application No. PCT/EP2015/052537, dated May 11, 2015, 14 pages.
Introducing Wii MotionPlus, Nintendo's upcoming accessory for the revolutionary Wii Remote, Nintendo, The Wayback Machine, Jul. 14, 2008, 2 pages.
Ireland et al., "3D Surface Imaging in Dentistry—What we are Looking at", British Dental Journal, vol. 205, No. 7, Oct. 11, 2008, pp. 387-392.
Jahne, et al., "Handbook of Computer Vision and Applications", Sensorsand Imaging, vol. 1, Academic Press, 1999, 657 pages.
Pulli, et al., "View-based Rendering: Visualizing Real Objects From Scanned Range and Color Data", In Rendering techniques'97, Springer, Vienna, 1997, pp. 23-34.
Record of Oral Hearing in IPR2018-00197, U.S. Pat. No. 9,329,675, Feb. 4, 2019, 67 pages.
Remondino, et al., "Image-Based 3D Modelling: A Review", The Photogrammetric Record, vol. 21, No. 115, Sep. 2006, pp. 269-291.
Reply Declaration of Lambertus Hesselink, Exhibit 1057.
Report and Recommendation, *3Shape A/S* v. *Align Technology, Inc.*, Case No. 1:18-886-LPS, May 6, 2020, 24 pages.
Richard J. Cherry "New Techniques of Optical Microscopy and Microspectroscopy", The Macmillan Press Ltd., 1991 (3 pages).
Sato Yoichi, "Object Shape and Reflectance Modeling from Color Image Sequence", The Robotics Institute Carnegie Mlellon University, Jan. 1997, 158 pages.
Savarese et al., "3D Reconstruction by Shadow Carving: Theory and Practical Evaluation", International Journal of Computer Vision, vol. 71, No. 3, Mar. 2007, pp. 1-48.
Schendel et al., "3D Orthognathic Surgery Simulation Using Image Fusion", Seminars in Orthodontics, vol. 15, No. 1, Mar. 2009, pp. 48-56 (11 pages).
Second Office Action dated Nov. 18, 2015, issued in the corresponding Chinese Patent Application No. 201180066956.6, 27 pages including 16 pages of English Translation.
Sinescu et al., "Laser Beam Used in Dental Scanning for CAD/CAM Technologies", TMJ, vol. 57, No. 2-3, 2007, pp. 187-191 (6 pages).
Slabaugh, "Novel Volumetric Scene Reconstruction Methods for New View Synthesis", PhD Thesis in Electrical and Computer Engineering at Georgia Institute of Technology, Nov. 2002, 209 pages.
Slabaugh, G.G., et al., "Methods for Volumetric Reconstruction of Visual Scenes", International Journal of Computer Vision, vol. 57, 2004, pp. 179-199.
Smith Warrenj., "Modem Optical Engineering: The Design of Optical Systems", Third Edition, Exhibit 1065, 2000, 105 pages.
Smith, "Digital Signal Processing: A Practical Guide for Engineers and Scientists," Demystifying Technology Series, pp. 138, 262, 307-308 (1998).
Spencer et al., "General Ray-Tracing Procedure", Journal of the Optical Society of America, vol. 52, No. 6, Jun. 1962, pp. 672-678.
Steele et al., "Bodies in Motion: Monitoring Daily Activity and Exercise with Motion Sensors in People with Chronic Pulmonary Disease", Journal of Rehabilitation Research & Development, vol. 40, No. 5, Suppl. 2, Oct. 2003, pp. 45-58.

(56) References Cited

OTHER PUBLICATIONS

Steinbach, et al., "3-D Object Reconstruction Using Spatially Extended Voxels and Multi-Hypothesis Voxel Coloring", In Proceedings 15th International Conference on Pattern Recognition, ICPR, vol. 1, IEEE, 2000, pp. 774-777.
Tang, et al., "Automatic Reconstruction of as-built Building Information Models from Laser-Scanned Point Clouds: A Review of Related Techniques, Automation in Construction 19", Automation in Construction, vol. 19, No. 7, Nov. 1, 2010, pp. 829-843.
Taxonomies of Input in Developing a Taxonomy of Input, (IPR2018-00197, Ex. 2010) Available at https://www.billbuxton.com/inputo4.Taxonomies.pdf., Jan. 4, 2009, 16 pages.
Tiziani et al., "Theoretical Analysis of Confocal Microscopy with Microlenses", Applied Optics vol. 35, Issue 1, Jan. 1, 1996, pp. 120-125 (7 pages).
Transcript of Alexander V. Sergienko, Ph.D., *Align Technology, Inc.* v. *3Shape A/S et al.*, Exhibit 1056, Jul. 16, 2021, 212 pages.
Transcript of Apr. 21, 2020 Video Claim Construction Hearing, *3Shape A/S* v. *Align Technology, Inc.*, Case No. 1:18-886-LPS, Apr. 21, 2020, 137 pages.
Tsukizawa, et al., "3D Digitization of a Hand-held Object with a Wearable Vision Sensor", Published in International Workshop on Computer Vision in Human-Computer Interaction, CVHCI 2004: Computer Vision in Human-Computer Interaction, 2004, pp. 129-141.
Turner Daniel, "Hack: The Nintendo Wii", MIT Technology Review, Jul. 1, 2007, 3 pages.
U.S. Appl. No. 10/744,869, (IPR2018-00197, Ex. 2005), 69 pages.
U.S. Pat. No. 9,329,675,"Declaration of Dr. Chandrajit L. Bajaj, Ph.D. in Support of Inter Partes Review", *Align Technology, Inc.* Petitioner v. *3Shape A/S* Patent Owner, Case IPR2018-00198, Ex. 1003, 123 pages.
U.S. Pat. No. 9,329,675,"PTAB Trial Certificate Inter Partes Review Certificate", IPR Trial No. IPR2018-00197, Oct. 25, 2019, 2 pages.
US RE48,221,"Petition (1 of 2) for Inter Partes Review", *Align Technology, Inc.*, Petitioner, *3Shape A/S*, Patent Owner, Case No. IPR2022-00144, 99 pages.
US RE48,221,"Petition (2 of 2) for Inter Partes Review", Align Technology, Inc., Petitioner, 3Shape A/S, Patent Owner, Case No. IPR2022-00145, 97 pages.
Vedula, et al., "Shape and Motion Carving in 6D", Proceedings of the IEEE Conference on Computer Vision and Pattern Recognition, 2000, 7 pages.
Vivid 910: Non-Contact 3-D Digitizer, www.minolta.com. (3 pages).
Vogt et al., "An AR System With Intuitive User Interface for Manipulation and Visualization of 3D Medical Data", Studies in Health Technology and Informatics, vol. 98, 2004., pp. 397-403.
Welch et al., "Motion Tracking: No Silver Bullet, but a Respectable Arsenal", IEEE Computer Grapllics and Applications, vol. 22, No. 6, Dec. 10, 2002, pp. 24-38.
Welch et al., "High-Performance Wide-Area Optical Tracking The HiBall Tracking System", Presence: Teleoperators and Virtual Environments, vol. 10, No. 1, Feb. 2001, pp. 1-22.
Westphal et al., "Correction of Geometric and Refractive Image Distortions in Optical Coherence Tomography Applying Fermat's Principle", Optics Express, vol. 10, No. 9, May 6, 2002, pp. 397-404.
Wilson et al., "Confocal Microscopy by Aperture Correlation", Optics Letters vol. 21, Issue 23,1996, pp. 1879-1881 (4 pages).
Wilson et al., "Dynamic Lens Compensation for Active Color Imaging and Constant Magnification Focusing", The Robotics Institute, Carnegie Mellon University, Pittsburgh, Pennsylvania 15213, Exhibit 2027, Nov. 1991, 52 pages.
Wilson et al., "Real-Time Three-Dimensional Imaging of Macroscopic Structures", Journal of Microscopy, vol. 191, No. 2, Aug. 1998, pp. 116-118.
Xia et al., "Three-Dimensional Virtual-Reality Surgical Planning and Soft-Tissue Prediction for Orthognathic Surgery", IEEE Transactions on Information Technology in Biomedicine, vol. 5, No. 2, Jun. 2001, pp. 97-107.

Xiao, et al., "Efficient Partial-Surface Registration for 3D Objects", Computer Vision and Image Understanding, vol. 98, No. 2, 2005, pp. 271-294.
Yamany et al., "Free-Form Surface Registration Using Surface Signatures", The Proceedings of the Seventh IEEE International Conference on Computer Vision, vol. 2, 1999, 7 pages.
Yang, et al., "Dealing with Textureless Regions and Specular Highlights—A Progressive Space Carving Scheme Using a Novel Photo-Consistency Measure", Proceedings of the Ninth IEEE International Conference on Computer Vision (ICCV 2003) 2—Volume Set, 2003, 9 pages.
Yoshida et al., "Intraoral Ultrasonic Scanning as a Diagnostic Aid", Journal of Cranio-Maxillofacial Surgery, vol. 15, 1987, pp. 306-311.
Yoshizawa Toru, "Handbook of Optical Metrology Principles and Application", Second Edition, Feb. 25, 2009, 15 pages.
Yuan et al., "Inferring 3D Volumetric Shape of Both Moving Objects and Static Background Observed by a Moving Camera", IEEE Conference on Computer Vision and Pattern Recognition, 2007, 8 pages.
Zhang et al., "A 3-dimensional Vision System for Dental Applications", Proceedings of the 29th Annual International, Aug. 23-26, 2007, pp. 3369-3372.
Agrawal, Color and Shade Management in Esthetic Dentistry, Dec. 1, 2013, 120-127, vol. 3, Issue 3.
Baltzer et al., "The Determination of the Tooth Colors", Quintessenz Zahntechnik, 30(7), 2004, 726-740.
Borse et al., Tooth shade analysis and selection in prosthodontics: A systematic review and meta-analysis, Apr. 7, 2020, J Indian Prosthodont Soc, 20, 131-140.
Chu, Dental Color Matching Instrument and Systems. Review of Clinical and Research Aspects, Journal of Dentistry, 2000, e2-e16, vol. 38, Supplement 2.
Complaint, 3Shape A/S v. Carestream Dental, LLC, Civil Action No. 6:21-cv-1110, WDTX, Oct. 26, 2021, 59 pages.
Corcodel et al., "Metameric effect between natural teeth and the shade tabs of a shade guide", May 11, 2010, European Journal of Oral Sciences, pp. 311-316.
Curriculum Vitae of Dr. Ioannis A. Kakadiaris (56 pages).
Curriculum Vitae of Dr. James L. Mullins (13 pages).
Declaration of Dr. James L. Mullins (94 pages).
Declaration of Ioannis A. Kakadiaris (104 pages).
Defendants Initial Invalidity Contentions (Ndga - Civil Action No. 1:22-cv-01829-WMR), dated Sep. 12, 2022 (92 pages).
Defendants' First Supplemental Invalidity Contentions (NDGA—Civil Action No. 1:22-cv-01829-WMR), dated Nov. 7, 2022 (101 pages).
DK priority document for Patent Application No. PA 2014 70066 (29 pages).
Douglas et al., "Intraoral determination of the tolerance of dentists for perceptibility and acceptability of shade mismatch", Apr. 1, 2007, Journal of Prosthetic Dentistry, 9(4), 200-208.
Gonzalez et al., Digital Image Processing, Pearson Prentice Hall, 2008, Third Edition (977 pages).
Ishikawa-Nagai et al., "Reproducibility of Tooth Color Gradation Using A Computer Color-Matching Technique Applied to Ceramic Restorations", J. Prosthetic Dentistry (Feb. 2005), pp. 129-137.
Kang, "Three-Dimensional Lookup Table with Interpolation", Computational Color Technology, Chapter 9, 2006, pp. 151-159.
Lagouvardos et al., "Repeatability and Interdevice Reliability of Two Portable Color Selection Devices in Matching and Measuring Tooth Color", J. Prosthetic Dentistry (2007), 40-45.
Netravali, Digital Pictures: Representation and Compression (Applications of Communications Theory), 1988.
Petition for Inter Partes Review of U.S. Pat. No. 10,695,151, dated Dec. 21, 2022 (87 pages).
Richert et al., Intraoral Scanner Technologies: A Review to Make a Successful Impression, Journal of Healthcare Engineering, 2017, 9 pages.
Schropp, Shade Matching Assisted by Digital Photography and Computer Software, Jan. 1, 2009, Journal of Prosthodontics, 235-241.
Tam, Dental Shade Matching Using a Digital Camera, Dec. 1, 2012, Journal of Dentistry, e3-e10, vol. 40, Supplement 2.

(56) References Cited

OTHER PUBLICATIONS

Toriwaki, et al., Fundamentals of Three-Dimensional Digital Image Processing, Springer, 2009, 278 pages.
Tung et al., "The Repeatability of an Intraoral Dental Colorimeter", Dec. 1, 2002, J. Prosthetic Dentistry, 585-590.
U.S. Office Action for U.S. Appl. No. 15/888,764 (8 pages).
Vadher, et al., Basics of Color in Dentistry: A Review, Sep. 1, 2014, IOSR Journal of Dental and Medical Sciences, 13(9), 78- 85.

* cited by examiner

DETECTING TOOTH SHADE

CROSS REFERENCE TO RELATED APPLICATIONS

The present application is a continuation of U.S. application Ser. No. 16/946,186, filed on Jun. 9, 2020, which is a continuation of U.S. application Ser. No. 15/888,764, filed on Feb. 5, 2018, now U.S. Pat. No. 10,695,151, which is a continuation of U.S. application Ser. No. 15/117,078, filed on Aug. 5, 2016, now U.S. Pat. No. 10,010,387, which is a U.S. national stage of International Application No. PCT/EP2015/052537, filed on Feb. 6, 2015, which claims the benefit of Danish Application No. PA 2014-70066, filed on Feb. 7, 2014. The entire contents of each of U.S. application Ser. No. 16/946,186, U.S. application Ser. No. 15/888,764, U.S. application Ser. No. 15/117,078, International Application No. PCT/EP2015/052537, and Danish Application No. PA 2014-700665 are hereby incorporated herein by reference in their entirety.

TECHNICAL FIELD

This invention generally relates to methods and a user interfaces for determining the shade of a patient's tooth or teeth and for utilizing the determined tooth shades for designing and manufacturing dental restorations.

When designing and manufacturing a dental restoration for a patient, such as a crown or a bridge restoration, it is advantageous that both the shape and shade of the manufactured restoration is adapted to the patient's natural teeth surrounding the restoration. If the shade of the restoration differs significantly from the surrounding natural teeth, e.g. is significantly darker or brighter than these, the restoration appear artificial and deteriorate the aesthetic impression of the patient's smile.

The tooth color can be represented in many different color spaces, such as the L*C*h* color space representing color in terms of Lightness, Chroma and Hue, or in the L*a*b* color space as described e.g. by Hassel et al. (Hassel 2012) and Dozic et al. (Dozic 2007). The L*a*b* color space has the advantage that it is designed to approximate human vision with the L* component closely matches human perception of lightness.

In order to aid dental technicians in their manual work of manufacturing a restoration which appears natural, the tooth colors are often expressed in terms of reference tooth shade values of a tooth shade system (often referred to as a tooth shade guide). Each reference tooth shade value in a tooth shade guide represents a predetermined and known tooth color value and often correspond to the color of commercially available ceramics for the production of dental restorations. This is e.g. the case for the VITA 3D-Master or the VITA Classic shade guides provided by VITA Zahnfabrik, Germany.

In the VITA 3D-Master system, tooth shades are expressed in codes referring to the L*C*h* color space, where each code is constructed according to (Lightness, hue, Chroma). One example of a tooth shade value is 3R1.5 where "3" refers to the lightness, "R" to the hue and "1.5" to the Chroma of the tooth. This allows the dentist to describe the shade of the patient's tooth in terms that a dental technician immediately understands, such that the technician will know from which ceramics he should manufacture the restoration to provide that it has the correct shade.

When manually determining which reference tooth shade value best matches the color of a patient's tooth, the dentist holds different pre-manufactured teeth of the shade guide at the tooth for comparison. Often a picture is taken with the pre-manufactured structures arranged at the teeth. The technician who produces the prosthetic then uses the picture in evaluating which ceramic must be used for the different parts of the restoration based on the picture. This process is both time consuming and inaccurate.

SUMMARY

Disclosed is a method for determining shade of a patient's tooth, wherein the method comprises:
  obtaining a digital 3D representation of the tooth, where the digital 3D representation comprises shape data and texture data for the tooth; and
  determining a tooth shade value for at least one point on the tooth based on the texture data of the corresponding point of the digital 3D representation and on known texture values of one or more reference tooth shade values.

Disclosed is a user interface for determining and displaying shade of a patient's tooth, wherein the user interface is configured for:
  obtaining a digital 3D representation of the tooth, said digital 3D representation comprising shape data and texture data for the tooth;
  displaying at least the shape data of the digital 3D representation such that the shape of the tooth is visualized in the user interface;
  determining a tooth shade value for at least one point on the tooth based on the texture data of the corresponding point of the digital 3D representation and on known texture values of one or more reference tooth shade values; and
  displaying the determined tooth shade value.

The texture data of the digital 3D representation expresses the texture of the tooth. The texture data can be a texture profile expressing the variation in the texture over the tooth. The shape data of the digital 3D representation expresses the shape of the tooth.

In some embodiments, the texture information comprises at least one of tooth color or surface roughness.

When the texture information comprises tooth color information, the texture data expressing a texture profile of the tooth may be color data expressing a color profile of the tooth, and the tooth shade value for a point on the tooth may be derived by comparing the color data of the corresponding point of the digital 3D representation with known color values of one or more reference tooth shade values.

Determining both the tooth shade value from a digital 3D representation comprising both shape data expressing the shape of the tooth and texture data expressing a texture profile of the tooth provides the advantage that shade and geometry information are directly linked. This e.g. advantageous e.g. in CAD/CAM dentistry where dental restorations are designed using Computer Aided Design (CAD) tools and subsequently manufactured from the design using Computer Aided Design (CAM) tools. The material used for the manufacture of the dental restoration can then be selected based on the determined tooth shade value.

In many cases, the dental restoration is manufactured with a shade profile where the shade differs from the incisal edge towards cervical end of the restoration. The disclosed invention allows the operator to determine tooth shade values for several points on the tooth such that a shade profile can be determined for the dental restoration. Multi-shaded milling blocks exits which mimics standard tooth shade profiles.

Having the shape data and the tooth shade values linked via the digital 3D representation provides that the correct portion of the multi-shaded milling block can be milled out. The remaining portion of the multi-shaded milling block forming the dental restoration will then have a shape and shade profile which closely resembles that of a natural tooth.

In some embodiments, obtaining the digital 3D representation of the tooth comprises recording a series of sub-scans of the tooth, where at least one of said sub-scans comprises both texture information and geometry information for said tooth, and generating the digital 3D representation of the tooth from the recorded series of sub-scans.

When a plurality of the sub-scans comprise texture information, the texture data for the digital 3D representation can be derived by combining the texture information of the several sub-scans.

The recorded sub-scans comprise at least data of the tooth for which the shade is determined, but potentially also of the neighboring teeth such that for example the shape and location of the neighboring teeth can be taken into account when designing a dental restoration for the tooth. Texture information and texture data for the neighboring teeth can also be used to determine the shade value for the tooth, e.g. by interpolation of the shades determined for the neighbor teeth.

In some embodiments, the method comprises creating a shade profile for the tooth from shade values determined for one or more of points on the tooth.

The shade profile of natural teeth often has a brighter shade at the incisal edge of the tooth and gradually changes into a darker shade towards the cervical end of the tooth, i.e. the end at the patient's gingiva.

When the tooth shade value is determined for one point only the tooth shade profile may be generated based on knowledge of the normal tooth shade profile for that particular type of tooth and patient. This knowledge may relate to how the shade profile normally changes over the tooth, the age and gender of the patients, etc.

Often the profile will be based on tooth shades determined in several points on the tooth to provide the most reliable tooth shade profile.

In some embodiments the user interface is configured for creating a shade profile for the tooth from tooth shade values determined for one or more points on the tooth.

In some embodiments, the tooth shade profile can be created by interpolation of tooth shade values determined for points distributed over the tooth surface with some distance between the points. The tooth shade value for some parts of the tooth surface are then not derived directly from sub-scan texture information relating to these parts but from the determined tooth shade values for other parts/points on the tooth surface. A tooth shade profile for the entire labial/buccal surface of the tooth can thus be created from a selection of points on the surface providing a fast and often sufficiently accurate procedure for creating the tooth shade profile. The interpolation of the tooth shade values can be realized by an interpolation in each of the coordinates of the color space used to describe the tooth color.

In some embodiments, the tooth shade profile comprises a one or more tooth shade regions on the tooth surface where an average tooth shade is derived for each region from tooth shade values determined for a number of points within the region.

The tooth shade region can be defined by a structure encircling a portion of the tooth surface in the digital 3D representation, where either the operator or a computer implemented algorithm decides where each geometric structure is located on the digital 3D representation. Different shapes (e.g. circles, squares, or rectangles) and sizes (e.g. corresponding to a few millimeters) of the geometric structure can be used. The number of points within the geometrical structure can be increased to provide a more accurate measure of the shade or reduced to provide a faster calculation.

The average tooth shade value for a region can e.g. be derived as a weighted average where the tooth shade value for points in the center of the structure is assigned a higher weight than tooth shade value of points closer to the boundary.

The tooth surface can also be divided into a coronal, a middle and a cervical region. Some natural teeth has a shade profile which can be expressed by such a division and many dentists and dental technicians are familiar with such a division In some embodiments, tooth shade values are determined for a plurality of teeth, i.e. on parts of the digital 3D representation corresponding to two or more teeth, and a tooth shade value and/or a tooth shade profile for each of these teeth is created from the determined tooth shade values.

In some embodiments, the texture data at least partly are derived by combining the texture information from corresponding parts of a number of the sub-scans.

The digital 3D representation can be generated through registration of sub-scans into a common coordinate system by matching overlapping sections of sub-scans, i.e. the sections of the sub-scans which relate to the same region of the tooth. When two or more sub-scans also comprise texture information relating to the same region of the tooth, deriving the texture data for this region in the digital 3D representation can comprise combining the corresponding texture information, i.e. the texture information in the sub-scans corresponding to the same sections of the tooth.

Deriving the texture data based on texture information from two or more sub-scan can provide a more accurate measurement of the texture data. The texture information of one sub-scan for a particular region of the tooth may be unreliable e.g. due to the angle between the surface in this region and the scanner when this particular sub-scan was recorded. The combination of texture information from several sub-scans can provide a more reliable color.

In some embodiments, combining the texture information from the sub-scans comprises interpolating the texture information, i.e. texture information from parts of the sub-scans corresponding to a point on the tooth are interpolated to determine the texture data for that point.

Such an interpolation can provide that the determined texture data is more accurate e.g. in cases where the texture information for a point on the tooth is not linearly varying over the sub-scans such that a simple averaging will not provide the best result.

In some embodiments, combining the texture information from the sub-scans comprises calculating an average value of the texture information, i.e. texture data for a point on the digital 3D representation are determined by averaging the texture information of the sub-scans corresponding to that point on the tooth.

In some embodiments, the calculated average value is a weighted average of the texture information.

This approach has the advantage that the derived texture data of the digital 3D representation are not as sensitive to errors in the texture information of a single sub-scan.

Such errors can be caused by several factors. One factor is the angle between the optical path of the probe light at the tooth surface and the tooth surface itself. When utilizing e.g. the focus scanning technique, the texture data for a point on the tooth is preferably derived from a number of sub-scans where at least some of the sub-scans are recorded at different orientations of the scanner relative to the teeth. The sections of the sub-scans relating to this point are hence acquired at different angles relative to the tooth surface in this point.

A portion of a sub-scan recorded from a surface perpendicular to the optical path of the probe light at the tooth may be dominated by specular reflected light which does not describe the texture of the tooth but rather the spectral distribution of the probe light. A portion of a sub-scan recorded from a tooth surface almost parallel to the optical path is often quite weak and hence often provide an erroneous detection of the texture at that point.

In some embodiments, the texture information from parts of a sub-scan relating to a tooth surface which is substantially perpendicular or parallel to the optical path are assigned a low weight in the weighted averaging of the texture information to determine the texture data for the point.

The orientation of the scanner relative to the tooth when a sub-scan is acquired can be determined from the shape of the sub-scan. Parts of the sub-scan relating to tooth surfaces which are substantially parallel or perpendicular to the optical path can thus immediately be detected in the sub-scan such that the texture information of the corresponding parts are assigned at low weight when determining the texture data for this point from a series of sub-scans.

A specular reflection from the tooth often has an intensity which is significantly higher than that of e.g. diffuse light from surfaces which have an oblique angle relative to the optical path. In some cases the specular reflection will saturate the pixels of the image sensor used for the recording of the sub-scans.

In some embodiments, the method comprises detecting saturated pixels in the recorded sub-scans and assigning a low weight to the texture information of the saturated pixels when combining the texture information from the sub-scans, i.e. when calculating the weighted average of the texture information.

Specular reflection from a tooth surface may also be detected from a comparison between the spectrum of the light received from the tooth and that of the probe light. If these spectra a very similar it indicates that the tooth has a perfectly white surface which is not natural. Such texture information may thus be assigned a low weight in a weighted average of texture information.

In some embodiments determining the tooth shade value for the point comprises selecting the reference tooth shade value with known texture value closest to the texture data of the point.

When the texture data comprises color data, selecting the tooth shade value of the point can comprise calculating the color difference between the determined color data in the point and the color data of the reference tooth shade values. This difference can e.g. be calculated as a Euclidian distance in the used color space. As an example, Dozic et al. (Dozic 2007) describes that the Euclidian distance $\Delta E$ between two points $(L^*_1, a^*_1, b^*_1)$ and $(L^*_2, a^*_2, b^*_2)$ in the $L^*a^*b^*$ color space is given by:

$$\Delta E = \sqrt[2]{(L^*_1 - L^*_2)^2 + (a^*_1 - a^*_2)^2 + (b^*_1 - b^*_2)^2}$$

Selecting the tooth shade value can then comprise determining for which of the reference tooth shades the color difference, i.e. the Euclidian distance, is the smallest.

In some embodiments determining the tooth shade value for the point comprises an interpolation of the two or more reference tooth shade values having known texture values close to the texture data of the point.

This interpolation provides that the tooth shade can be represented with a more detailed solution than what is provided by the tooth shade standard used to describe the tooth shade. For instance when using a Lightness-Hue-Chroma code a tooth shade value of 1.5M2.5 can be determined for the tooth by interpolation of Lightness values of 1 and 2, and Chroma values of 2 and 3.

The tooth shade value can be displayed in a user interface e.g. together with the digital 3D representation of the tooth. If the digital 3D representation also contains parts relating to other teeth the tooth shade value for the tooth is preferably displayed at the tooth, such as at the point of the for which the tooth shade value has been determined.

The tooth shade value can also be represented as a color mapped onto the digital 3D representation.

When a dental restoration is designed based on the determined tooth shade value this can provide a visualization of how the restoration will appear together with neighboring teeth also contained in the digital 3D representation obtained by scanning the teeth.

In some embodiments, the method comprises deriving a certainty score expressing the certainty of the determined tooth shade value.

Deriving a certainty score for the determined tooth shade value provides the advantage that a measure of how accurate the determined value is can be displayed to the operator, preferably when the patient is still at the clinic such that further scanning can be performed if this is required to provide a more precise tooth shade value.

In some embodiments, the method comprises generating a visual representation of the certainty score and displaying this visual representation in a user interface.

In some embodiments, the method comprises generating a certainty score profile at least for a portion of the tooth, where the certainty scope profile represents the certainty scores for tooth shade values determined for a number of points on the tooth, such as for the values in a tooth shade profile for the tooth. The certainty score profile can be mapped onto the digital 3D representation of the tooth and visualized in a user interface. When the tooth shade profile also is mapped onto the tooth digital 3D representation the operator may be allowed to toggle between having the tooth shade profile and having the certainty scope profiled visualized on the digital 3D representation.

In some embodiments the visual representation of the certainty score is displayed together with or is mapped onto the digital 3D representation of the tooth.

In some embodiments, the method comprises comparing the derived certainty score with a range of acceptable certainty score values. This is done to verify that the certainty score is acceptable, i.e. that the determined tooth shade value is sufficiently reliable.

One boundary of the range can be defined by a threshold value. When a high certainty scope indicates that the determined shade value most likely is correct, the threshold value may define the lower boundary of the range and vice versa.

A visual representation of the certainty score or of the result of the comparison of the certainty score with the range can be generated and displayed in a user interface. Preferably, this visual representation is displayed together with the determined tooth shade value.

In some embodiments, the method comprises deciding based on the certainty score whether the determined tooth shade value or tooth shade profile is acceptable. This may be based on the comparison of the derived certainty score and the range of acceptable certainty score values, e.g. where it is decided that the determined tooth shade value is acceptable if the certainty score is within the range of acceptable values.

In some embodiments, the certainty measure relates to how uniform the sub-scan texture information is at the point.

If large variations are found in the texture information in the vicinity of the parts corresponding to the point for a substantial fraction of the sub-scans, the texture data derived therefrom may be unreliable and the tooth shade value derived for this point is accordingly not very reliable.

In some embodiments, the certainty measure relates to how close the texture data is to the known texture value of the determined tooth shade value. In particular, the certainty measure may relate to how close one parameter of the color data of the digital 3D representation is to the corresponding parameter of the known color for the determined tooth shade value. For example, the certainty measure may relate to the difference in the lightness parameter between point of the digital 3D representation and the determined tooth shade value.

The Euclidian distance between the color data to the selected reference tooth shade value can also be used in determining the certainty measure. If the Euclidian distance is above a threshold value the uncertainty is then evaluated to be too large. The color data can here both relate to color data of the point or the average color data for a region surrounding the point.

In some embodiments, the certainty measure relates to the amount of texture information used to derive the texture data at the point.

When the texture data for the point is derived from a limited amount of texture information the texture data, and accordingly the tooth shade value derived therefrom, may be less reliable than the tooth shade values derived from large amounts of texture information.

In some embodiments, the visual representation of the certainty score comprises a binary code, such as red for certainty scores outside a range of acceptable certainty score values, and green for certainty scores within the range, a bar structure with a color gradient, a numerical value, and/or a comparison between the texture data and the known texture value of the determined tooth shade value.

In some embodiments, the visual representation of the certainty score comprises a certainty score indicator.

The certainty score indicator may comprise a bar structure with a color gradient going from a first color representing a low certainty score to a second color representing a high certainty score. The first color may be red and the second color green. The color gradient of the bar structure may be configured to have an intermediate color, e.g. yellow representing the threshold value for the certainty score. The certainty score indicator may comprise marker which is arranged relative to the color gradient of the bar structure such that it indicated the certainty score.

In some embodiments, the visual representation of the certainty score comprises a numerical value, such as a numerical value in an interval extending from a lower limit indicating a low certainly, i.e. a relatively uncertain tooth shade value, to a higher limit indicating a high certainty, i.e. a relatively certain tooth shade value.

In some embodiments, the one or more reference tooth shade values relate to shade values for natural teeth with intact surface and/or to shade values for teeth prepared for a dental restoration.

The reference tooth shade values used for determining the tooth shade can be selected based on the tooth. Intact and healthy teeth normally have tooth shades in one range of tooth shade values where a tooth prepared for a dental restoration has a tooth shade in another range, which may overlap with the range for healthy teeth. It may thus be advantageous that the operator enters whether the tooth is intact or prepared for a restoration and the appropriate color space is used in the comparison with the texture data.

If the color data in the point on the digital 3D representation of the tooth has a poor match to all the reference tooth shade values of the selected tooth shade system/guide the point may e.g. be on the gingiva of the patient or relate to silver filling.

In some embodiments, the method comprises comparing the texture data with known texture values for soft oral tissue, such as gum tissue and gingiva.

This may e.g. be relevant when the certainty scores are outside said range of acceptable certainty score values for all tooth shade values of a tooth shade system, i.e. if there is a poor match between the texture data and the known texture for all the tooth shades of the reference set.

In a user interface for implementing the method, it may be suggested to the operator that the point perhaps is not on a tooth surface but on the gums or gingiva of the patient. This suggestion may be provided both when the texture data has been found to give a good match with known texture values of gum/gingiva and/or when the texture data has a poor match with the known texture values of the reference tooth shade values in the tooth shade system or systems.

In some embodiments, the method comprises determining an alternative tooth shade value for the point when said certainty score is outside said range of acceptable certainty score values.

In some embodiments, the method comprises displaying the alternative tooth shade value in the user interface optionally together with the digital 3D representation of the patient's set of teeth and/or the initially determined tooth shade value The digital 3D representation of the tooth is generated at least partly from the geometry information of the sub-scans. In some embodiments, the texture information of the sub-scans is also taken into account when generating the digital 3D representation of the tooth.

Sub-scans comprising texture information and geometry information may be recorded for more than said tooth, such that the generated digital 3D representation may comprise shade data expressing the shape and texture data expressing the texture profile of several of the patient's teeth.

Disclosed is a method for determining shade of a patient's tooth, wherein the method comprises:
  recording a series of sub-scans of the patient's set of teeth, where a plurality of said sub-scans comprises both texture information and geometry information for said tooth;
  generating a digital 3D representation of the tooth from said sub-scans, wherein the digital 3D representation comprises shape data expressing the shape of the tooth and texture data expressing a texture profile of the tooth; and
  determining a tooth shade value for a point on the tooth by comparing the texture data of the corresponding point of the digital 3D representation with a known texture value of one or more reference tooth shade values.

Disclosed is a user interface for determining and displaying shade of a patient's tooth, wherein the user interface is configured for:

obtaining a digital 3D representation of the tooth, said digital 3D representation comprising shape data expressing the shape of the tooth and texture data expressing a texture profile of the tooth;

displaying at least the shape data of the digital 3D representation such that the shape of the tooth is visualized in the user interface;

determining a tooth shade value for a point on the tooth by comparing the texture data of the corresponding point of the digital 3D representation with a known texture value of one or more reference tooth shade values; and displaying the determined tooth shade value.

In some embodiments, the user interface is configured for deriving a certainty score expressing the certainty of the determined tooth shade value for said point.

In some embodiments, the user interface comprises a virtual tool which when activated on a point of the digital 3D representation of the tooth provides that the determined tooth shade value for the point; and/or a visual representation of a certainty score for the determined tooth shade value; and/or a visual representation of a comparison of the derived certainty score with a range of acceptable certainty score values is visualized in the user interface.

The user interface can then provide the operator with an opportunity to decide based on the visualized certainty score and/or the visual representations whether the determined tooth shade value or tooth shade profile is acceptable.

In some embodiments, the visual representation of the comparison of the derived certainty score with the range of acceptable certainty score values comprises a binary code, such as red for certainty scores outside a range of acceptable certainty score values, and green for certainty scores within the range. Other means for this visualization are described above.

The visualized certainty score and/or the representation(s) of the certainty score or comparison of the certainty score with the range of acceptable certainty score values may be displayed at the digital 3D representation in the user interface or in a shade value region of the user interface.

In some embodiments, the user interface is configured for determining an alternative shade value for the point and for displaying the alternative shade value when the certainty scores outside a range of acceptable certainty score values.

Disclosed is a method for designing a dental restoration for a patient, wherein the method comprises:

obtaining a digital 3D representation of at least one tooth, said digital 3D representation comprising shape data expressing the shape of the tooth and texture data expressing a texture profile of the tooth;

determining a tooth shade value for a point on the tooth by comparing the texture data of the corresponding point of the digital 3D representation with a known texture value of one or more reference tooth shade values; and creating a digital restoration design for one or more of the patient's teeth; and selecting a restoration shade of the digital restoration design based on said tooth shade value.

The digital restoration design can e.g. be for the manufacture of dental prosthetic restoration for the patient, such as a crown or a bridge restoration, where the digital restoration design expresses a desired shape and shade profile of the dental restoration. Such digital restoration designs can be in the form of a CAD model of the dental restoration.

In some embodiments, the method comprises suggesting a dental material for manufacturing the dental restoration from the digital restoration design based on the determined restoration shade.

In cases where the dental restoration is designed and manufactured for an existing tooth which has an acceptable shade, the tooth shade value or tooth shade profile can be determined for the existing tooth and the shade of the digital restoration design based on the tooth shade value or tooth shade profile of the existing tooth.

This may e.g. be advantageous for the crown portions of a bridge restoration in the case where the tooth which is intended to accept the crown portion of the bridge is a healthy tooth.

In some cases the dental restoration is designed and manufactured for a tooth which either is damaged or has an undesired shade profile, such as for a broken or dead tooth. In such cases it can be advantageous to determine the tooth shade value or tooth shade profile for one or more of the neighboring teeth and selecting the restoration shade of the digital restoration design from e.g. an interpolation of the tooth shade values/profiles of the neighboring teeth.

Disclosed is a method for designing a dental restoration for a first tooth, wherein the method comprises:

obtaining a digital 3D representation of the patient's set of teeth, said digital 3D representation comprising shape data and texture data expressing the shape and texture profile, respectively, of at least one second tooth;

designing a digital restoration design for the first tooth;

deriving a desired texture profile of the digital restoration design from the texture data of the at least one second tooth; and determining a restoration shade value or restoration shade profile of the digital restoration design by comparing the desired texture profile with texture values for one or more reference tooth shade values.

In some embodiments, the desired texture profile is derived by interpolation or averaging of the texture data of the digital 3D representation of the neighbor teeth.

In some embodiments, one or more of the sub-scans comprise texture information for the patient's soft tissue, and optionally geometry information for said soft tissue. The generated digital 3D representation may then comprise shape data expressing the shape of the soft tissue and texture data expressing a texture profile of the soft tissue.

From this information, an aesthetica) pleasing denture can be designed where the color of the soft tissue part of the denture is selected based on the texture profile of the corresponding part of the digital 3D representation.

Knowledge of the texture of the soft tissue, such as of the color of the soft tissue, can also be used for diagnostics. When the texture data of a point on the digital 3D representation corresponding to soft tissue does not provide a sufficiently good match with a known range of texture values for soft tissue, a warning may be prompted in a user interface to alert the operator that the soft tissue is suspicious.

Disclosed is a system for determining shade of a patient's tooth, wherein the system comprises:

a scanner capable of recording a digital 3D representation of the tooth, where the digital 3D representation comprises shape data and texture data for the tooth; and a data processing system comprising a computer-readable medium having stored thereon the program code means for causing the data processing system to determine a tooth shade value for at least one point on the tooth based on the texture data of the corresponding point of the digital 3D representation and on known texture values of one or more reference tooth shade values using the method according to any of the embodiments.

In some embodiments, the sub-scans are recorded using an intra-oral scanner, such as the 3Shape TRIOS intra-oral scanner.

The intra-oral scanner may be configured for utilizing focus scanning, where the sub-scans of the scanned teeth are reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the maximum of a correlation measure for each of a plurality of the sensor elements or each of a plurality of groups of the sensor elements for a range of focus planes as described in WO2010145669. From the in-focus positions, sub-scans of the set of teeth can be derived with geometry information relating to the shape of the scanned surface. When e.g. the image sensor is a color sensor and the light source provides a multispectral signal a plurality of the sub-scans can include both geometry information and texture information, such as color information, for said tooth.

A digital 3D representation of the set of teeth can then be generated from the recorded sub-scans by e.g. the use of an Iterative Closest Point (ICP) algorithm. Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

The generated digital 3D representation formed by such a procedure comprises shape data expressing the shape of the tooth. The texture information of the sub-scans can be used in various ways to provide that the generated digital 3D representation also comprises texture data expressing a texture profile of the tooth. For a number of the sub-scans, the part of the sub-scan relating to the same point on the tooth can be identified, e.g. during the ICP procedure. The corresponding texture information of these parts of the sub-scans can then be combined to provide the texture data for that point.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

The present invention relates to different aspects including the method and user interface described above and in the following, and corresponding methods and user interface, each yielding one or more of the described advantage, and each having one or more embodiments corresponding to the embodiments described above and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
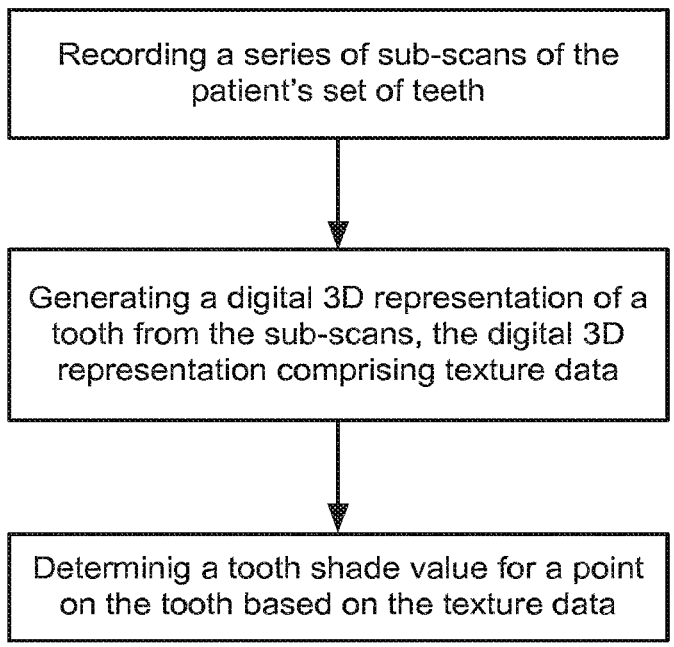
FIG. 1 shows an example of a flow chart for an embodiment.

FIG. 1 shows an example of a flow chart 100 for an embodiment of the method for determining shade of a patient's tooth.

In step 102 a series of sub-scans of the patient's set of teeth is recorded, where a plurality of said sub-scans comprises both texture information and shape information for the tooth.

In step 103 a digital 3D representation of the tooth is generated from said sub-scans, where the digital 3D representation comprises texture data expressing a texture profile of the tooth. The digital 3D representation further comprises shape data expressing the shape of the tooth such that the shape of the tooth can be visualized in a user interface.

In step 104 a tooth shade value for a point on the tooth is determined based on the texture data. This is done at least in part by comparing the texture data of the corresponding point of the digital 3D representation with a known texture value of one or more reference tooth shade values. The reference tooth shade values may be provided in the form of a library file and comprise tooth shade values and corresponding texture values based on e.g. the VITA 3D-Master and/or the VITA Classic tooth shade systems.

Figure 2:
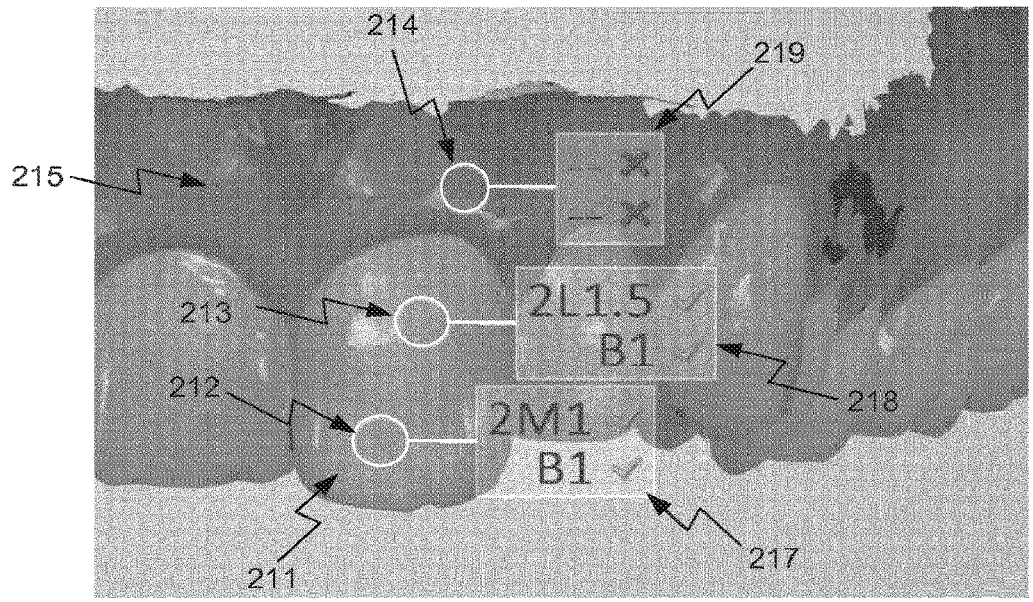
FIGS. 2 to 4 show parts of screen shots of user interfaces.
Figure 3:
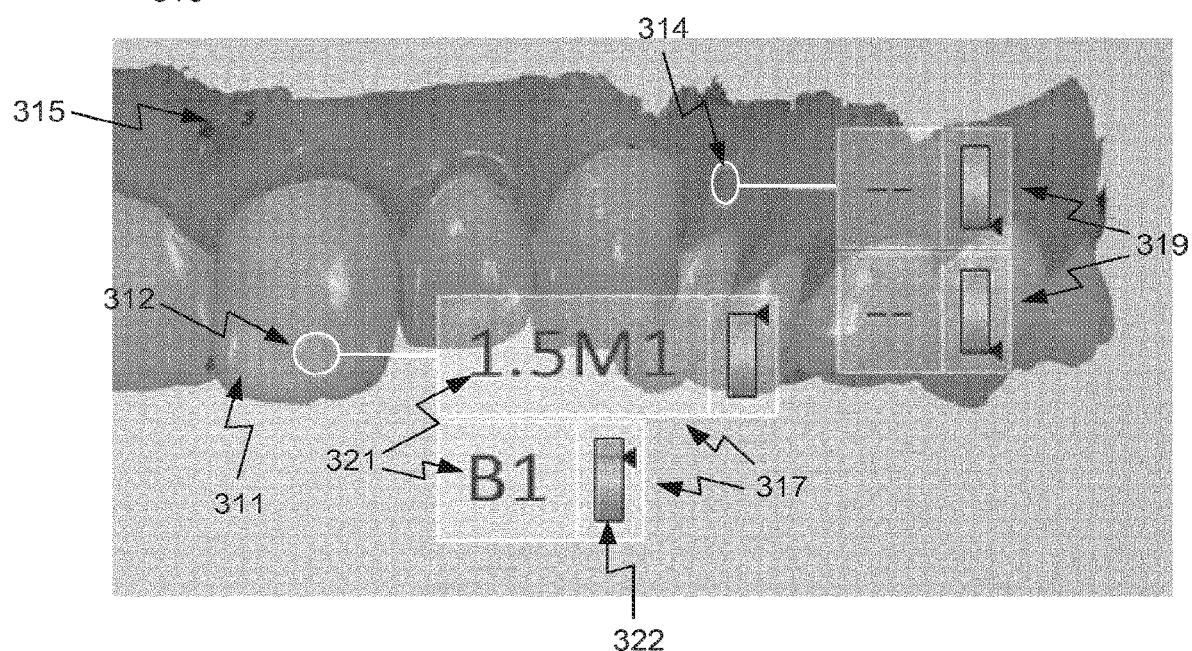
Figure 4:
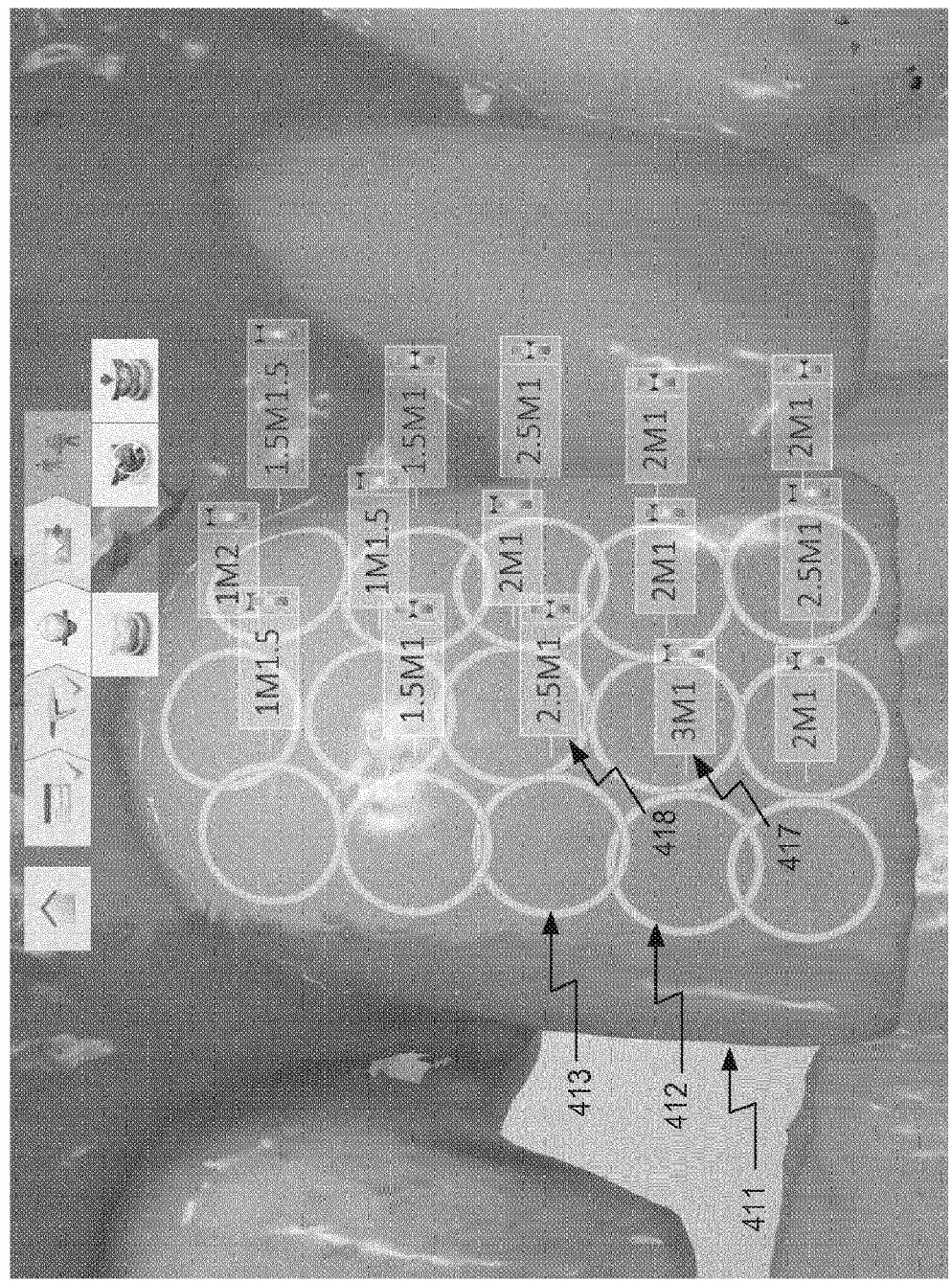

FIGS. 2 to 4 show parts of screen shots from user interfaces in which derived tooth shade values and visual representation of the corresponding certainty scores for a number of tooth regions are displayed at the digital 3D representations of the patient's set of teeth.

The point or points on the tooth for which the tooth shade value(s) is/are determined can be selected by an operator. This can be the case e.g. when the digital 3D representation of the tooth is visualized in a user interface and the operator uses a pointing tool, such as a computer mouse, to indicate where on the digital 3D representation of the tooth, he wishes to determine the tooth shade value. The point or points can also be selected by a computer implemented algorithm based on predetermined positions on the digital 3D representation of the tooth, such as a point arranged at a certain distance to the incisal edge of the tooth.

The screen shot 210 seen in FIG. 2 shows three regions 212, 213, 214 on the digital 3D representation of the patient's set of teeth. Two of these 212, 213, are selected at the part of the digital 3D representation corresponding to the tooth 211 while the third 214 is selected on the soft tissue part 215 of the digital 3D representation. Average tooth shade value for a region can be calculated by averaging over tooth shade values derived for a number of points within the region or by calculating an average texture value for the region and determining the average tooth shade value therefrom. The average tooth shade values are displayed in tooth value sections 217, 218, 219 linked to the regions in the user interface. In the tooth value sections 217, 218 relating to the regions 212, 213 two tooth shade values are displayed where the upper shade value is derived using known texture values corresponding to the reference tooth shade values of the VITA 3D-Master tooth shade system and the lower tooth shade values relates to the VITA Classic tooth shade system. It is also seen that for the region 213 closest to the gingiva, the tooth shade is determined to be 2L1.5 in the VITA 3D-Master system and B1 in the VITA Classic system. In FIG. 2 the certainty scores for the derived tooth shade values are visualized as a certainty score indicator displayed next to the tooth shade values. In FIG. 2 the visualization of the certainty score indicator is in the form of a checkmark which indicates that the certainty score is sufficiently good to provide that the derived tooth shade values can be relied upon. The color of the checkmark may provide further information to the certainty score, such as in cases where a green checkmark indicates a more certain tooth shade value than a yellow checkmark. The third region 214 is located at the patient's soft tissue. An anatomical correct tooth shade value can hence not be calculated from the texture data of that part of the digital 3D representation of the patient's teeth and the corresponding certainty scope is accordingly very low. The visualization of the certainty score in the tooth value section 219 is hence a cross indicating that the derived shade value was rejected. Further no shade value is indicated in the tooth value section 219.

The screen shot 310 seen in FIG. 3 shows two regions 312, 314 on the digital 3D representation of the patient's set of teeth. One of these regions 312 is selected at the part of the digital 3D representation corresponding to the tooth 311 while the second region 314 is selected on the soft tissue part 315 of the digital 3D representation. Average tooth shade value for a region can be calculated as described above in relation to FIG. 2. Shade value sections 317, 319 are also displayed for the regions 312, 314. Two tooth shade values 321 are derived for the region 312 and displayed in the corresponding tooth value section 317, where the upper value is derived using known texture values corresponding to the reference tooth shade values of the VITA 3D-Master tooth shade system (derived tooth shade value is 1.5M1) and the lower value using the VITA Classic tooth shade system (derived tooth shade value is B1). In FIG. 3 the certainty score is visualized in the form of a certainty score indicator 322 comprising a vertical bar with a color gradient going from red representing a poor certainty score to green representing a good certainty score. The certainty score indicator has a marker indicating the certainty score on the bar. It is seen that the tooth shade value 1.5M1 of the VITA 3D-Master system is more certain than the tooth shade value B1 of the VITA Classic system for this region. The tooth shade value of 1.5M1 is found by interpolation of the reference tooth shades 1M1 and 2M2.

The second region 314 is located at the patient's soft tissue. An anatomical correct tooth shade value can hence not be calculated from the texture data of that part of the digital 3D representation of the patient's teeth and the corresponding certainty scope is accordingly very low as seen in the vertical bars of tooth value section 319.

FIG. 4 shows a screen shot 410 where determined tooth shade values are derived for a total of 15 regions on the digital 3D representation of the tooth 411. The tooth shade values are all derived based on the known texture values of the reference tooth shade values of the VITA 3D-Master tooth shade system. The certainty scores are visualized in the form of a certainty score indicator comprising a vertical bar with a color gradient going from red representing a poor certainty score to green representing a good certainty score. As can be seen in the tooth value sections 417, 418 of the user interface there are large variations in the certainty scores. For example, the certainty score for the region 412 is almost at maximum while the certainty score of the region 413 is much close to a threshold for acceptable certainty score values. When tooth shade values are determined for a number of points on the tooth, the points may be arranged in a grid over the part of the digital 3D representation of the tooth.

Figure 5:
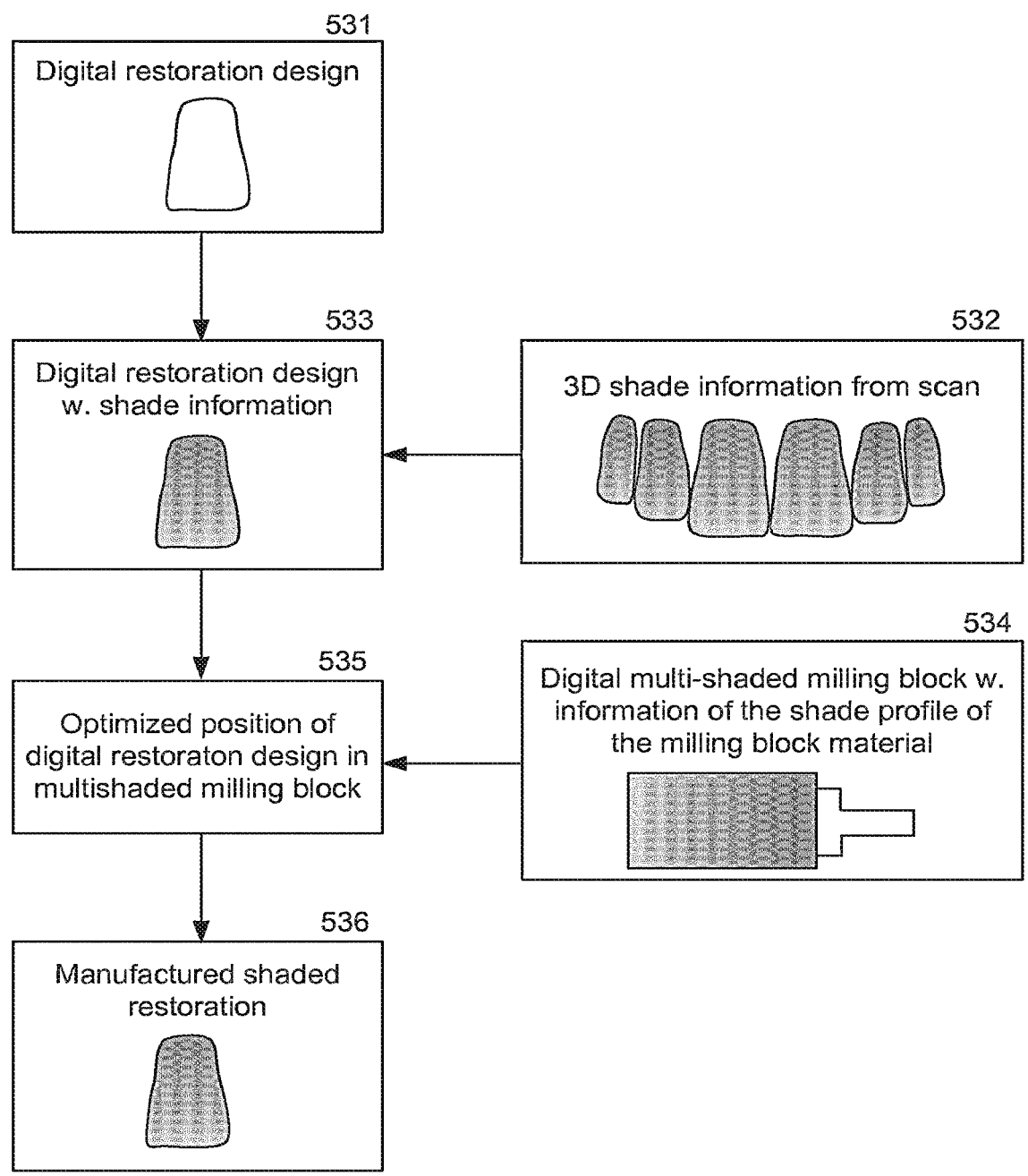
FIG. 5 shows steps of a method for designing a dental restoration.

FIG. 5 shows steps of a method for designing a dental restoration.

In step 531 a digital restoration design is created e.g. based on the shape data of a digital 3D representation of the patient's set of teeth and/or on template digital restoration design loaded from a library. Template digital restoration designs may e.g. be used when the tooth is broken.

In step 532 the tooth shade values of different points or regions of the teeth are derived from the texture data of the digital 3D representation of the patient's set of teeth. From the derived tooth shade values or from tooth shade profiles created based on the derived tooth shade values a desired shade profile for the dental restoration can be determined. This can be based on e.g. feature extraction where shade values are extracted from the other teeth by e.g. identifying shade zones on these teeth and copying these zones to the dental restoration. It can also be based on established shade rules for teeth, e.g. a rule describing a relation between the tooth shades values or profiles of the canines and the anterior teeth.

In step 533 the desired tooth shade value(s) for the dental restoration is merged into the digital restoration design.

When the dental restoration is to be drilled from a multicolored milling block it is important that the dental restoration is milled from the correct parts of the milling block. In step 534 a CAD model of the milling block is provided, where the CAD model comprises information of the shade profile of the milling block material. The optimal position of the digital restoration design relative to the CAD model of the milling block is then determined in 535, where different criteria can be apply to provide the best fit between the desired shade profile and what actually can be obtained as dictated by the shade profile of the milling block.

In step 536 the dental restoration is manufactured from the milling block by removing milling block material until the dental restoration is shaped according to the digital restoration design.

Figure 6:
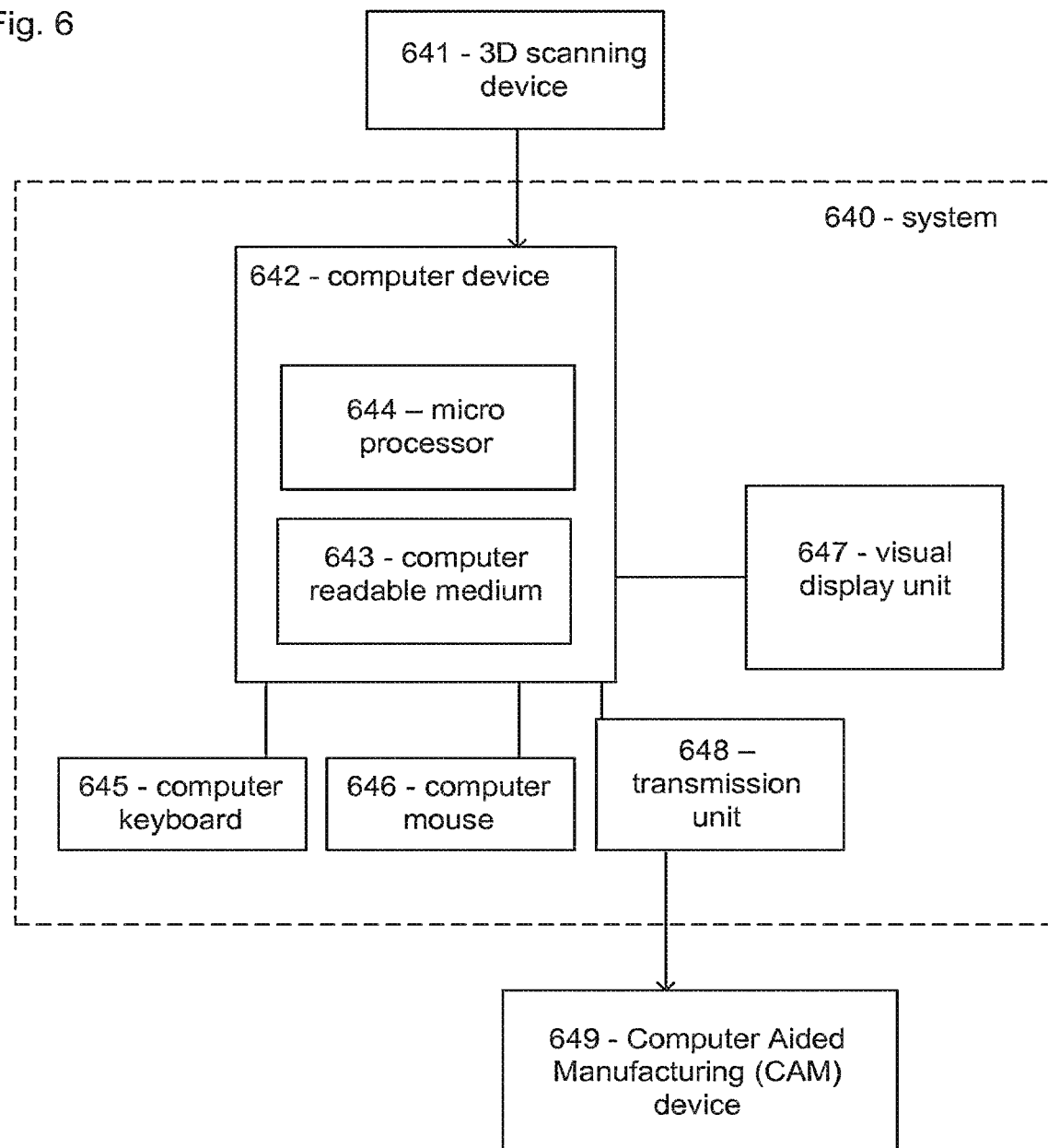
FIG. 6 shows a schematic of a system for determining tooth shade values

FIG. 6 shows a schematic of a system for determining tooth shade values. The system 640 comprises a computer device 642 comprising a computer readable medium 643 and a processor 644. The system further comprises a visual display unit 647, a computer keyboard 645 and a computer mouse 646 for entering data and activating virtual buttons in a user interface visualized on the visual display unit 647. The visual display unit can be a computer screen. The computer device 642 is capable of receiving a digital 3D representation of the patient's set of teeth from a scanning device 641, such as the TRIOS intra-oral color scanner manufactured by 3 shape A/S, or capable of receiving scan data from such a scanning device and forming a digital 3D representation of the patient's set of teeth based on such scan data. The obtained digital 3D representation can be stored in the computer readable medium 643 and provided to the processor 644. The processor is configured for implementing the method according to any of the embodiments. This may involve presenting one or more options to the operator, such as where to derive the tooth shade value and whether to accept a derived tooth shade value. The options can be presented in the user interface visualized on the visual display unit 647.

Many scanning devices have Bayer color filters with Red, Green and Blue filters and hence record color information in the RGB color space. For instance a focus scanner can record series of 2D color images for the generation of sub-scans, where the color information is provided in the RGB color space. The processor 644 then comprises algorithms for transforming the recorded color data into e.g. the L*a*b or L*C*h color spaces.

The system may further comprise a unit 648 for transmitting a digital restoration design and a CAD model of a milling block to e.g. a computer aided manufacturing (CAM) device 649 for manufacturing a shaded dental restoration or to another computer system e.g. located at a milling center where the dental restoration is manufactured. The unit for transmitting the digital restoration design can be a wired or a wireless connection.

The scanning of the patient's set of teeth using the scanning device 641 can be performed at a dentist while deriving the tooth shade values can be performed at a dental laboratory. In such cases the digital 3D representation of the patient's set of teeth can be provided via an internet connection between the dentist and the dental laboratory.

FIGS. 7A-7D and 8A-8B show schematics of intra-oral scanning.

Different scanner configurations can be used to acquire sub-scans comprising both shape and texture information. In some scanner designs the scanner is mounted on axes with encoders which provides that the sub-scans acquired from different orientations can be combined using position and orientation readings from the encoders. When the scanner operates by the focus-scanning technique the individual sub-scans of the tooth are derived from a sequence of 2D images obtained while scanning a focus plane over a portion of the tooth. The focus scanning technique is described in detail in WO2010145669. The shape information of the sub-scans for an object, such as a tooth, can be combined by algorithms for stitching and registration as widely known in the literature. Texture data relating to the tooth color can be obtained using a scanner having a multi-chromatic light source, e.g. a white light source and a color image sensor. Color information from multiple sub-scans can be interpolated and averaged by methods such as texture weaving, or by simply averaging corresponding color components of the sub-scans corresponding to the same point/location on the surface. Texture weaving is described by e.g. Callieri M, Cignoni P, Scopigno R. "Reconstructing textured meshes from multiple range rgb maps". VMV 2002, Erlangen, Nov. 20-22, 2002.

Figure 7A:
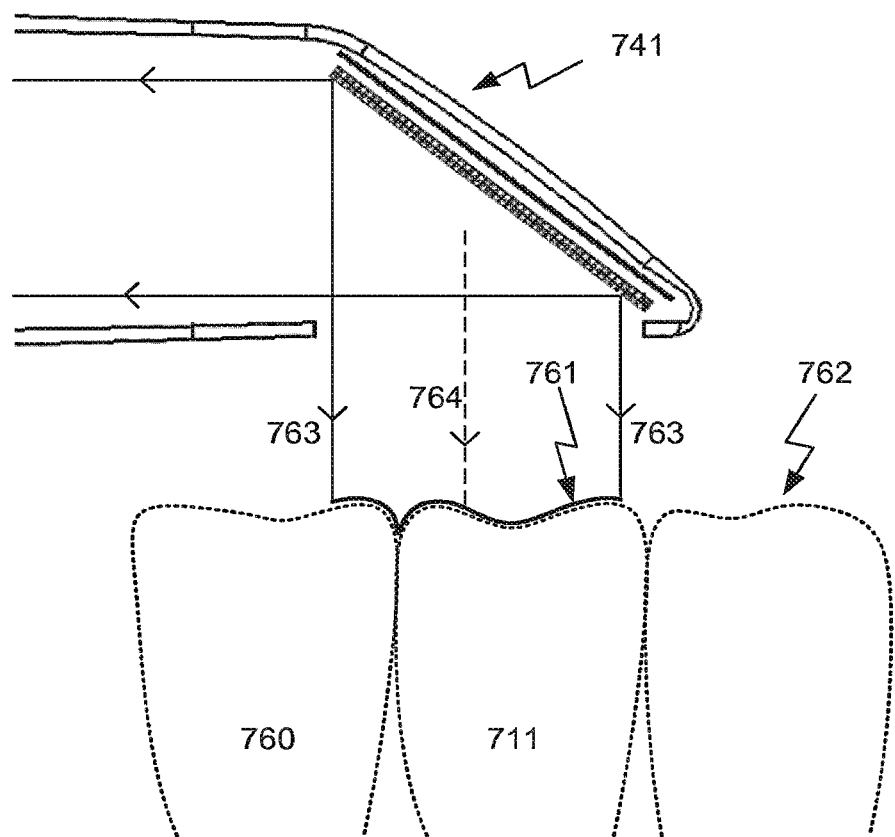
FIGS. 7A-7D and 8A-8B show schematics of intra-oral scanning.

In FIG. 7A the scanner 741 (here represented by a cross-sectional view of the scanner tip) is held in one position relative to the teeth 711, 760 (also represented by a cross-sectional view) while recording a sequence of 2D images for one sub-scan. The illustrated teeth can e.g. be the anterior teeth in the lower jaw. The size of the Field of View (here represented by the full line 761 on the teeth) of the scanner is determined by the light source, the optical components and the image sensor of the scanner. In the illustrated example, the Field of View 761 covers part of the surface of the tooth 711 and part of the surface of the neighbor tooth 760. The generated digital 3D representation can thus also contain data for the neighbor teeth. This is often advantageous, e.g. when the generated digital 3D representation is used for creating a digital restoration design for the manufacture of a dental restoration for the tooth. In the Figure, the scanner is arranged such that the acquired sub-scan comprises shape and color information for the incisal edge 762 of the teeth. The probe light rays 763 from the scanner corresponding to the perimeter of the Field of View are also shown in the Figure. These probe light rays 763 define the optical path 764 of the scanner probe light at the tooth 711.

Figure 7B:
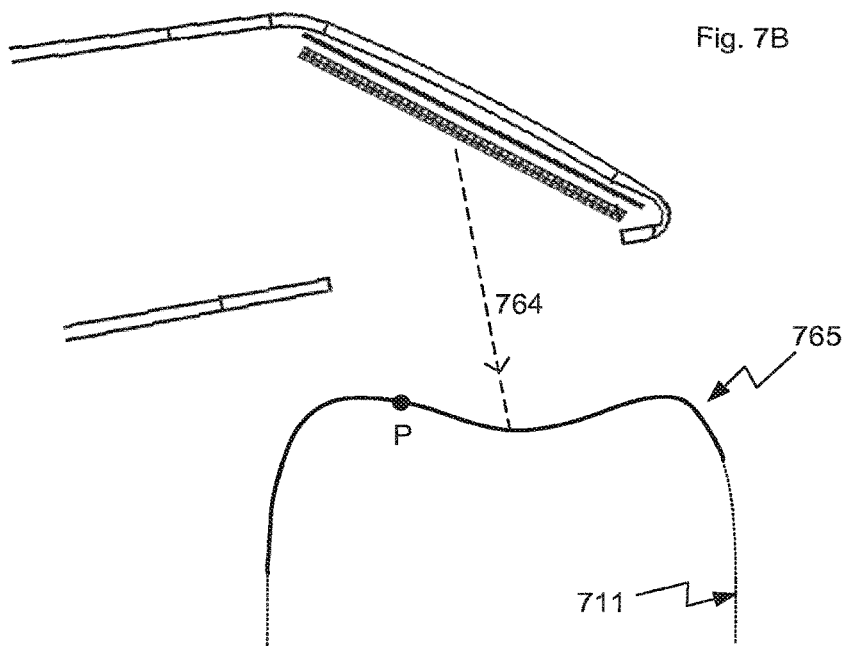
Figure 7C:
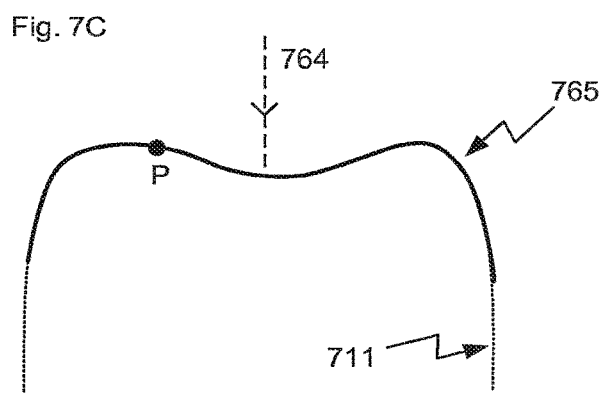
Figure 7D:
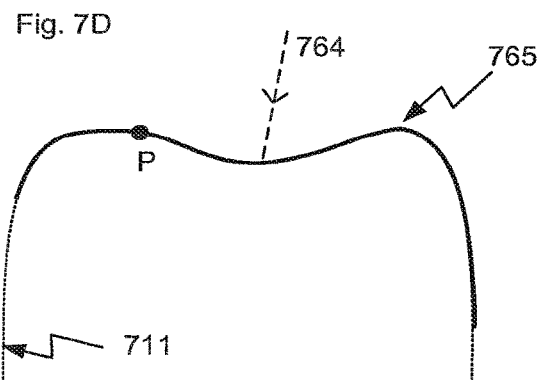

A digital 3D representation of the tooth can be generated by combining sub-scans acquired from different orientations relative to the teeth, e.g. by sub-scan registration. Sub-scans acquired from three such different orientations are illustrated in FIGS. 7B, 7C and 7D, where only the optical path 763 of the scanner probe light is used to represent the relative scanner/tooth orientation in FIGS. 7C and 7D. The sub-scans (here represented by the full line 765 on the teeth) covers different but overlapping sections of the tooth surface such that the sub-scans can be combined by registration into a common coordinate system using e.g. an Iterative Closest Point (ICP) algorithm as described above. A segment of each of the sub-scans corresponds to the point P on the tooth surface. When the sub-scans are registered to generate a digital 3D representation of the tooth, a correlation between these segments is established and the texture information of these sub-scan segments can be combined to determine the texture data for point P on the generated digital 3D representation of the tooth.

One way of doing this is to calculate the average value for each of the parameters used to describe the texture. For example, when the L*a*b* color system is used to describe the color information provided in each sub-scan, the color data of the digital 3D representation can be derived by averaging over each of the L*, a*, and b* parameters of the sub-scans. For example, the L* parameter of the color data for a given point P is then given by L $$(P) = \frac{1}{N}\sum_{i}^{N}$$

$L^*_i(P)$ where N is the number of sub-scans used in deriving the texture data and $L^*_i(P)$ is the L* parameter of the i'th sub-scan for the segment relating to P. Equivalent expressions are true for the a* and b* parameters for point P. The color parameters for each point on the digital 3D representation of the tooth can be determined for sections of or the entire surface of the tooth, such that the generated digital 3D representation comprises both shape and texture information about the tooth. The spatial resolution of the color data does not necessarily have to be identical to the resolution of the shape data of the digital 3D representation. The point P can be described e.g. in Cartesian, cylindrical or polar coordinates.

When the color data is derived for a point on the tooth, the tooth shade value for that point can be determined by comparing the derived color data with the known color data of the reference tooth shade values of a tooth shade guide such as the VITA 3D-Master.

Figure 8A:
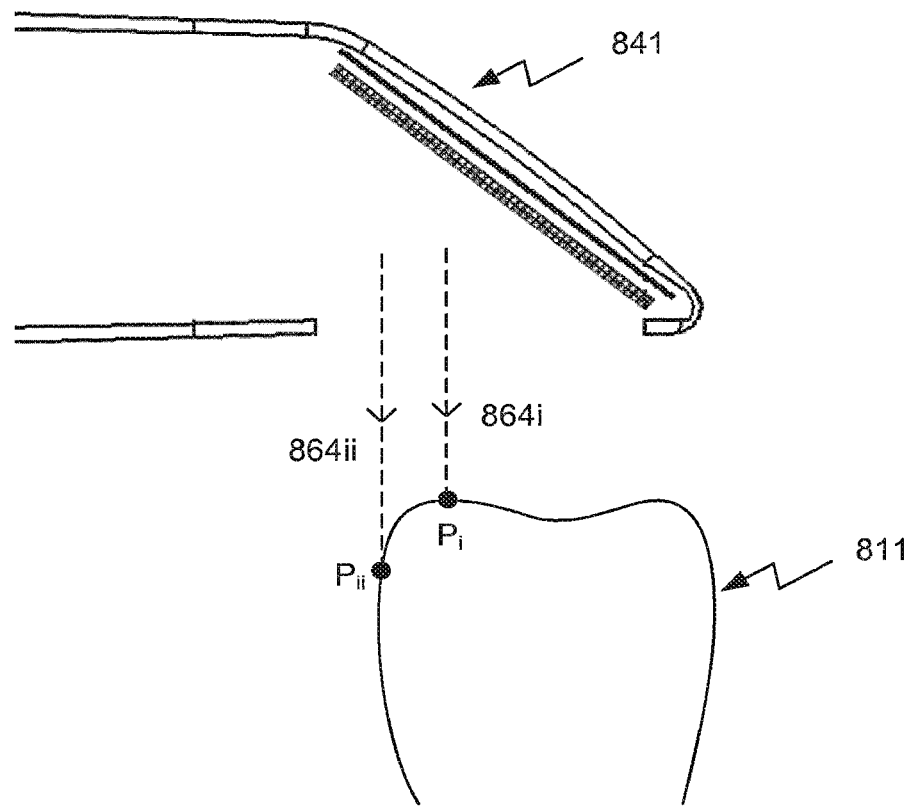
Figure 8B:
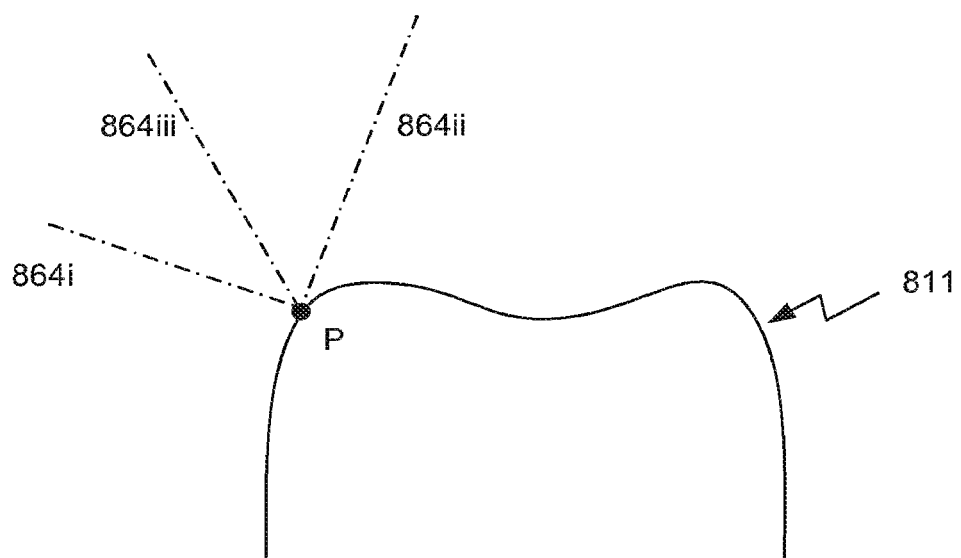

FIG. 8A-8B illustrates some potentially problematic tooth surface areas for particular arrangements of the scanner 841 relative to the tooth 811.

FIG. 8A shows two points $P_i$ and $P_{ii}$ on the tooth 811 where the tooth surface is either substantially perpendicular or parallel to the optical path, such that the texture information recorded at $P_i$ and $P_{ii}$ may be unreliable. This is because the tooth surface at $P_i$ is perpendicular to the optical path 864i at point $P_i$ which introduces the risk of having specular reflections of the probe light. The optical path 864ii at point $P_{ii}$ is parallel to the tooth surface at $P_{ii}$ such that the signal recorded from this part of the tooth surface in this sub-scan is relatively weak. This may cause that the color information in this section of the sub-scan are unreliable.

In order to obtain more precise color data the averaging of the color information described above in relation to FIG. 7 can be a weighted averaging where the color information of unreliable sub-scans segments are assigned a lower weight than others.

In FIG. 8B is indicated three different optical paths 864i, 864ii and 864iii at which sub-scans are acquired. When combining the color information for point P the color information of the segments of the sub-scans recorded with optical paths 864i and 864ii should be given a lower weight that the color information of the segment of the sub-scan recorded with the optical path 864iii.

This can be expressed by a modification of the equation given above. For a weighted averaging of the color information, the L* parameter of the color data for a given point P is given by $$L^*(P) = \sum_i^N \{\alpha_i(P) \cdot L_i^*(P)\} \bigg/ \sum_i^N \alpha_i$$

where $\alpha_i(P)$ is the weight factor for the color information of the i'th sub-scan in the segment at P. When a given sub-scan (e.g. the j'th sub-scan) is recorded at an angle relative to the tooth surface which causes the optical path to be e.g. perpendicular to the tooth surface at P, the corresponding weight factor $\alpha_i(P)$ is given a lower value than the color data of sub-scans acquired with an oblique angle between the optical path and the tooth surface.

Equivalent equations are true for the a* and b* parameters of the color data for point P.

Figure 9A:
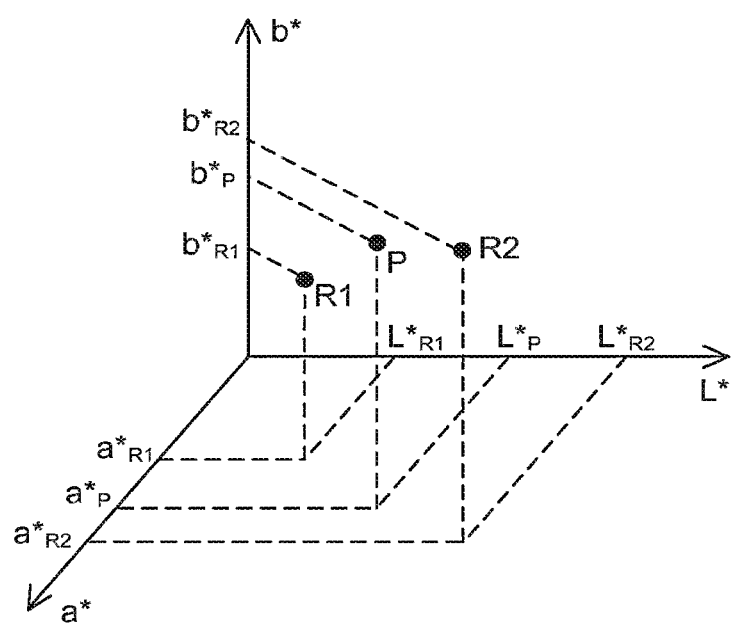
FIGS. 9A-9B illustrates one way of determining tooth shade values from texture data.

FIG. 9A=9B illustrates how a tooth shade value for a point P on a tooth can be determined based on reference tooth shade values.

For a given point P on the digital 3D representation, the color data $(L^*_p, a^*_p, b^*_p)$ has been determined, e.g. by combining the color information of a series of sub-scans used for generating the digital 3D representation. If the color information originally is recorded using the RGB color space it is transformed into the L*a*b* color space using algorithms known to the skilled person.

In the example illustrated by FIG. 9A, the color data of the digital 3D representation and the known color values of the reference tooth shades are expressed in the L*a*b* color space, and the reference tooth shades are those from the VITA classical shade guide.

The reference shade values of the Vita classical shade guide are: B1, A1, B2, D2, A2, C1, C2, D4, A3, D3, B3, A3.5, B4, C3, A4, and C4. The color data of these reference shades can be provided by scanning the corresponding pre-manufactured teeth of the shade guide. These color data are then also initially obtained in the RGB color space and can be converted to the L*a*b color space using the same algorithms applied to the color information/data for the point P.

The tooth shade value for the point is determined as the reference tooth shade value which has the smallest Euclidian distance to the point in the L*a*b color space. The Euclidian distance $\Delta E_{P-Ri}$ from the color $(L^*_p, a^*_p, b^*_p)$ to the known colors of the reference tooth shade values are calculated using the expression:

$$\Delta E_{P-Ri} = \sqrt[2]{(L^*_P - L^*_{Ri})^2 + (a^*_P - a^*_{Ri})^2 + (b^*_P - b^*_{Ri})^2}$$

where Ri refers to the i'th reference tooth shade.

In FIG. 9A only the known colors $(L^*_{R1}, a^*_{R1}, b^*_{R1})$ and $(L^*_{R2}, a^*_{R2}, b^*_{R2})$ for the two closest reference values R1 and R2, respectively, are illustrated for simplicity. It can be seen that the Euclidian distance in the color space from P to R2 is the smallest, and the tooth shade in point P is hence selected as that of R2.

The certainty score for the tooth shade value determined for point P depends on how close the color data of the point P is to the known color value of the selected reference tooth shade value. This can be quantified by the Euclidian distance and since point P is not particularly close to R2 in FIG. 9A the determined tooth shade has a poor certainty value.

An alternative approach to using the Euclidian distance is to determine individual parameters of the tooth shade value one at a time. This approach can be used e.g. when the reference tooth shades values are those of the Vita 3D-master system.

The reference tooth shade values of the Vita 3D-master shade guide are expressed in codes consisting of the three parameters Lightness-hue-Chroma, where Lightness is given in values between 1 and 5, the Chroma in values between 1 and 3, and the hue as one of "L", "M", or "R". A shade code in the Vita 3D-master can e.g. be 2M1, where the Lightness parameter equals 2, the Chroma 1 and the hue "M".

The known color data of the VITA 3D-master shade guide reference shades can be provided by scanning the pre-manufactured teeth of the shade guide. These color data are then also initially obtained in the RGB color space and can be converted to the L*a*b color space using the same algorithms applied to the color information/data for the point P. The known color data of each reference shade guide (having a code expressed in terms of Lightness, hue and Chroma) is then provided in terms of the L*a*b color space.

Since the lightness L has the largest impact on the human perception of the tooth color, the value of the Lightness-parameter $L^*_p$ in the point is determined first. The value of $L^*_p$ is compared with the values of the L* parameters for the reference tooth shades. If $L^*_p$ is close to the L*-value for the i'th reference tooth shade value, $L^*_{Ri}$ the L* parameter for point P may be set equal to $L^*_{Ri}$.

Figure 9B:
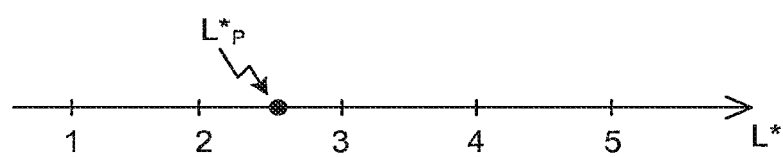

In some cases the Lightness parameter is not close to any of the references but instead is located almost in the middle between two L*-values. For example when $L^*_p$ in the point is between the values of $L^*_{Ri}=2$ and $L^*_{Ri+1}=3$ with almost equal distance to each of these as illustrated in FIG. 9B. Since the L*a*b color space is a linear space, the individual parameters of the shade values can be interpolated such that the Lightness for point P, $L^*_p$, can be set to 2.5.

The same procedure is performed for first the Chroma parameter and finally for the hue such that the three parameter of the tooth shade value are determined.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

REFERENCES

Hassel 2012: Hassel et al. "Determination of VITA Classical shades with the 3D-Master shade guide" Acta Odontol Scand. 2013; 71(3-4): 721-6.
Dozic 2007: Dozic et al. "Performance of five commercially available tooth color-measuring devices", J Prosthodont. 2007; 16(2):93-100.

EMBODIMENTS

1. A method for determining shade of a patient's tooth, wherein the method comprises:
    obtaining a digital 3D representation of the tooth, where the digital 3D representation comprises shape data and texture data for the tooth; and
    determining a tooth shade value for at least one point on the tooth based on the texture data of the corresponding point of the digital 3D representation and on known texture values of one or more reference tooth shade values.
2. The method according to embodiment 1, wherein determining the tooth shade value for the point comprises selecting the reference tooth shade value with the known texture value closest to the texture data of the point.
3. The method according to embodiment 1 or 2, wherein determining the tooth shade value for the point comprises an interpolation of the two or more reference tooth shade values having known texture values close to the texture data of the point.
4. The method according to any one of the preceding embodiments, wherein the method comprises deriving a certainty score expressing the certainty of the determined tooth shade value.
5. The method according to embodiment 4, wherein the method comprises generating a visual representation of the certainty score and displaying this visual representation in a user interface.
6. The method according to embodiment 5, wherein the visual representation of the certainty score is displayed together with or is mapped onto the digital 3D representation of the tooth.
7. The method according to any one of embodiments 4 to 6, wherein the method comprises comparing the derived certainty score with a range of acceptable certainty score values.
8. The method according to any one of embodiments 4 to 7, wherein the certainty measure relates to how uniform the sub-scan texture information is at the point, and/or to how close the texture data is to the known texture value of the determined tooth shade value, and/or to the amount of texture information used to derive the texture data at the point.
9. The method according to any one of embodiments 4 to 8, wherein the visual representation of the certainty score comprises a binary code, a bar structure with a color gradient, a numerical value, and/or a comparison between the texture data and the known texture value of the determined tooth shade value.
10. The method according to any one of the preceding embodiments, wherein the one or more reference tooth shade values relate to shade values for natural teeth with intact surface and/or to shade values for teeth prepared for a dental restoration.
11. The method according to any one of the preceding embodiments, wherein the method comprises comparing the texture data with known texture values for soft oral tissue, such as gum tissue and gingiva.
12. The method according to any of the previous embodiments, wherein the texture information comprises at least one of tooth color or surface roughness.
13. The method according to any one of the preceding embodiments, wherein the method comprises creating a shade profile for the tooth from shade values determined one or more points on the tooth.
14. The method according to embodiment 13, wherein the tooth shade profile comprises a one or more tooth shade regions on the tooth surface where an average tooth shade is derived for each region from tooth shade values determined for a number of points within the region
15. The method according to any of the previous embodiments, wherein obtaining the digital 3D representation of the tooth comprises recording a series of sub-scans of the tooth, where at least one of said sub-scans comprises both texture information and geometry information for said tooth, and generating the digital 3D representation of the tooth from the recorded series of sub-scans.

16. The method according to embodiment 15, wherein the texture data at least partly are derived by combining the texture information from corresponding parts of a number of the sub-scans.

17. The method according to embodiment 16, wherein combining the texture information from the sub-scans comprises interpolating the texture information and/or calculating an average value of the texture information.

18. The method according to embodiment 17, wherein the calculated average value is a weighted average of the texture information.

19. A user interface for determining and displaying shade of a patient's tooth, wherein the user interface is configured for:
    obtaining a digital 3D representation of the tooth, said digital 3D representation comprising shape data and texture data for the tooth;
    displaying at least the shape data of the digital 3D representation such that the shape of the tooth is visualized in the user interface;
    determining a tooth shade value for at least one point on the tooth based on the texture data of the corresponding point of the digital 3D representation and on known texture values of one or more reference tooth shade values; and displaying the determined tooth shade value.

The invention claimed is:

1. A non-transitory computer-readable medium having one or more computer-executable instructions stored thereon that, when executed by at least one processor of a computing device, cause the at least one processor to perform steps comprising:
    obtaining a digital 3D representation of a tooth based on scan data provided by an intraoral scanner, where the digital 3D representation comprises shape data and texture data for the tooth;
    determining a tooth shade value for at least one point on the tooth based on the texture data of the corresponding digital point of the digital 3D representation and on one or more reference tooth shade values; and
    deriving a certainty score expressing certainty of the determined tooth shade value.

2. The computer-readable medium according to claim 1, wherein determining the tooth shade value for the point comprises selecting the reference tooth shade value closest to the texture data of the point.

3. The computer-readable medium according to claim 1, wherein determining the tooth shade value for the point comprises an interpolation of two or more reference tooth shade values close to the texture data of the corresponding digital point.

4. The computer-readable medium according to claim 1, wherein the at least one processor is further caused to perform steps comprising generating a visual representation of the certainty score and displaying the visual representation in a user interface.

5. The computer-readable medium according to claim 4, wherein the visual representation of the certainty score is displayed together with or is mapped onto the digital 3D representation of the tooth.

6. The computer-readable medium according to claim 1, wherein the certainty score is based at least in part on at least one of a uniformity of a set of sub-scan texture information is at the corresponding digital point, the proximity of the texture data to the reference tooth shade and the amount the set of sub-scan of texture information used to derive the texture data at the corresponding digital point.

7. The computer-readable medium according to claim 1, wherein the at least one processor is further caused to perform steps comprising creating a shade profile for the tooth from one or more tooth shade values determined at one or more points on the tooth.

8. A non-transitory computer-readable medium comprising one or more computer-executable instructions that, when executed by at least one processor of a computing device, cause the at least one processor to perform steps comprising:
    obtaining a digital 3D representation of the tooth based on scan data provided by an intraoral scanner, where the digital 3D representation comprises shape data and texture data for the tooth;
    determining a tooth shade value for at least one point on the tooth based on the texture data of the corresponding point of the digital 3D representation and on known texture values of one or more reference tooth shade values; and
    creating a shade profile for the tooth from at least one tooth shade values,
    wherein the tooth shade profile includes a one or more tooth shade regions on the tooth each having an average tooth shade based at least in part on tooth shade values for a set of points within the tooth shade region.

9. A non-transitory computer-readable medium having one or more computer-executable instructions stored thereon that, when executed by at least one processor of a computing device, cause the at least one processor to perform steps comprising:
    recording a series of sub-scans, wherein at least one sub-scan of the series of sub-scans includes shape data and texture data for the tooth,
    generating a digital 3D representation of the tooth based at least in part on the series of sub-scans of the tooth, where the digital 3D representation includes shape data and texture data for the tooth; and
    determining a tooth shade value for at least one point on the tooth based on the texture data of a corresponding point of the digital 3D representation and on one or more reference tooth shade values.

10. The computer-readable medium according to claim 9, wherein the texture data of the digital 3D representation is at least partly are derived by combining the texture data from corresponding parts of at least two sub-scans of the series of sub-scans.

11. The computer-readable medium according to claim 10, wherein combining the texture data from the at least two sub-scans includes at least one of interpolating between the texture data of at least two sub-scans and calculating an average value of the texture data of at least two sub-scans.

12. The computer-readable medium according to claim 9, wherein the at least one processor is further caused to perform steps comprising:
    determining an indicator that represents the reliability of the tooth shade value; and
    causing display of the indicator in proximity to a display of the tooth shade value.

13. The computer-readable medium according to claim 9, wherein the at least one processor is further caused to perform steps comprising:
    causing display of a user interface;
    causing display of the digital 3D representation including a set of soft tissue on the user interface; and causing display of a warning on the user interface if the point is corresponds with the set of soft tissue.

14. The computer-readable medium according to claim 9, wherein the at least one processor is further caused to perform steps comprising:
causing display of a user interface;
causing display of the digital 3D representation including a set of soft tissue on the user interface; and
preventing display of the tooth shade value on the user interface if the point corresponds to the soft tissue.

15. A non-transitory computer-readable medium having one or more computer-executable instructions stored thereon that, when executed by at least one processor of a computing device, cause the at least one processor to perform steps comprising:
obtaining a digital 3D representation of the tooth based at least in part on scan data provided by an intraoral scanner, where the digital 3D representation includes shape data and texture data for the tooth;
determining a tooth shade value for at least one point on the tooth based at least in part on the texture data of a corresponding digital point of the digital 3D representation and on one or more reference tooth shade values;
deriving an indicator representing a reliability of the tooth shade value; and
displaying the indicator on a user interface next to the tooth shade value.

* * * * *